(12) United States Patent
Aguilar et al.

(10) Patent No.: US 10,065,154 B2
(45) Date of Patent: Sep. 4, 2018

(54) NANOFLUIDIC SORTING SYSTEM FOR GENE SYNTHESIS AND PCR REACTION PRODUCTS

(71) Applicant: Massachusetts Institute of Technology, Cambridge, MA (US)

(72) Inventors: Carlos Andres Aguilar, Boston, MA (US); Tarun Kumar Jain, New York, NY (US); Rohit N. Karnik, Cambridge, MA (US); Peter A. Carr, Medford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 735 days.

(21) Appl. No.: 14/433,471

(22) PCT Filed: Oct. 4, 2013

(86) PCT No.: PCT/US2013/063404
§ 371 (c)(1),
(2) Date: Aug. 27, 2015

(87) PCT Pub. No.: WO2014/105246
PCT Pub. Date: Jul. 3, 2014

(65) Prior Publication Data
US 2015/0283514 A1      Oct. 8, 2015

Related U.S. Application Data

(60) Provisional application No. 61/710,155, filed on Oct. 5, 2012.

(51) Int. Cl.
*B01D 61/44* (2006.01)
*B01D 69/02* (2006.01)
(Continued)

(52) U.S. Cl.
CPC .......... *B01D 69/02* (2013.01); *B01D 61/44* (2013.01); *B01D 63/005* (2013.01);
(Continued)

(58) Field of Classification Search
None
See application file for complete search history.

(56) References Cited

U.S. PATENT DOCUMENTS 7,468,271 B2   12/2008   Golovchenko et al.
2005/0103713 A1   5/2005   Ramsey et al.
(Continued)

FOREIGN PATENT DOCUMENTS

WO    WO 2012/065480    5/2012

OTHER PUBLICATIONS

Kovarik et al., Integrated Nanopore/Microchannel Devices for ac Electrokinetic Trapping of Particles. Anal Chem. Feb. 1, 2008;80(3):657-64.
(Continued)

Primary Examiner — Arun S Phasge
(74) Attorney, Agent, or Firm — Wolf, Greenfield & Sacks, P.C.

(57) ABSTRACT

Devices and methods integrate nanopore and microfluidic technologies for recording molecular characteristics of individual molecules such as, for example, biomolecules. Devices comprise a first substrate comprising a microchannel, a second substrate comprising a microchannel, the second substrate positioned below the first substrate, and a membrane having a thickness of about 0.3 nm to about 1 nm and comprising at least one nanopore, the membrane positioned between the first substrate and the second substrate, wherein a single nanopore of the membrane is constructed and arranged for electrical and fluid communication between the microchannel of the first substrate and the microchannel
(Continued)

of the second substrate. To mitigate the effect of errors that occur during de novo DNA synthesis, longer DNA molecules are typically synthesized from shorter oligonucleotides by polymerase construction and amplification (PCA), or by other methods.

32 Claims, 10 Drawing Sheets

(51) Int. Cl.
    *G01N 33/487*     (2006.01)
    *B01D 63/00*     (2006.01)
    *B01D 67/00*     (2006.01)
    *B01D 71/02*     (2006.01)
    *G01N 15/12*     (2006.01)
    *G01N 15/10*     (2006.01)
    *B01D 69/12*     (2006.01)
    *B32B 37/26*     (2006.01)
    *G01N 27/447*     (2006.01)
    *B01L 3/00*     (2006.01)
    *G01N 15/00*     (2006.01)

(52) U.S. Cl.
    CPC ....... *B01D 67/009* (2013.01); *B01D 67/0088* (2013.01); *B01D 69/125* (2013.01); *B01D 71/02* (2013.01); *B32B 37/26* (2013.01); *G01N 15/1056* (2013.01); *G01N 15/12* (2013.01); *G01N 27/44756* (2013.01); *G01N 33/48721* (2013.01); *B01D 2323/30* (2013.01); *B01D 2325/028* (2013.01); *B01D 2325/26* (2013.01); *B01L 3/502761* (2013.01); *G01N 2015/0038* (2013.01); *G01N 2015/1081* (2013.01)

(56) References Cited

U.S. PATENT DOCUMENTS

| | | | |
|---|---|---|---|
| 2006/0169588 | A1 | 8/2006 | Jacobson et al. |
| 2007/0217957 | A1 | 9/2007 | Flachsbart et al. |
| 2012/0080313 | A1 | 4/2012 | Baumgart et al. |
| 2013/0240378 | A1 | 9/2013 | Lee et al. |
| 2014/0374255 | A1* | 12/2014 | Hongo ............... G01N 15/1218 204/518 |

OTHER PUBLICATIONS

Zhang, Combined Nanochannel-Nanopore Device for Single-Molecule DNA Analysis and Manipulation. Thesis. McGill University. Montreal, Quebec. May 2, 2012. 84 pages.
[No Author Listed] Microfluidic Valve Technology. Stanford University. Retrieved from www.stanford.edu/group/foundry/microfluidicvalvetechnology.html on Aug. 22, 2012.
Ahn et al., Heterogeneous three-dimensional electronics by use of printed semiconductor nanomaterials. Science. Dec. 15, 2006;314(5806):1754-7.
Bao et al., Microfluidic electroporation for selective release of intracellular molecules at the single-cell level. Electrophoresis. Jul. 2008;29(14):2939-44. doi: 10.1002/elps.200700856.
Ben Yehezkel et al., De novo DNA synthesis using single molecule PCR. Nucleic Acids Res. Oct. 2008;36(17):e107. doi: 10.1093/nar/gkn457. Epub Jul. 30, 2008.
Branton et al., The potential and challenges of nanopore sequencing. Nat Biotechnol. Oct. 2008;26(10):1146-53. doi:10.1038/nbt.1495.
Chang et al., DNA-Mediated Fluctuations in Ionic Current through Silicon Oxide Nanopore Channels. Nano Letters. 2004;4(8):1551-1556.
Chen et al., Atomic Layer Deposition to Fine-Tune the Surface Properties and Diameters of Fabricated Nanopores. Nano Lett. Jun. 25, 2004;4(7):1333-1337.
Chen et al., DNA translocation through an array of kinked nanopores. Nat Mater. Aug. 2010;9(8):667-75. doi:10.1038/nmat2805.
Chou et al., A microfabricated device for sizing and sorting DNA molecules. Proc Natl Acad Sci U S A. Jan. 5, 1999;96(1):11-3.
Chu et al., Real-time monitoring of DNA polymerase function and stepwise single-nucleotide DNA strand translocation through a protein nanopore. Angew Chem Int Ed Engl. Dec. 27, 2010;49(52):10106-9. doi: 10.1002/anie.201005460.
Cipriany et al., Real-time analysis and selection of methylated DNA by fluorescence-activated single molecule sorting in a nanofluidic channel. Proc Natl Acad Sci U S A. May 29, 2012;109(22):8477-82. doi: 10.1073/pnas.1117549109. Epub May 14, 2012.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Dekker, Solid-state nanopores. Nat Nanotechnol. Apr. 2007;2(4):209-15. doi:10.1038/nnan0.2007.27. Epub Mar. 4, 2007.
Dimitrov et al., Nanopores in solid-state membranes engineered for single molecule detection. Nanotechnology. Feb. 10, 2010;21(6):065502. doi:10.1088/0957-4484/21/6/065502. Epub Jan. 11, 2010.
Fologea et al., DNA conformation and base number simultaneously determined in a nanopore. Electrophoresis. Sep. 2007;28(18):3186-92.
Fologea et al., Slowing DNA translocation in a solid-state nanopore. Nano Lett. Sep. 2005;5(9):1734-7.
Fu et al., A patterned anisotropic nanofluidic sieving structure for continuous-flow separation of DNA and proteins. Nat Nanotechnol. Feb. 2007;2(2):121-8. doi: 10.1038/nnano.2006.206.
Iqbal et al., Solid-state nanopore channels with DNA selectivity. Nat Nanotechnol. Apr. 2007;2(4):243-8. doi: 10.1038/nnano.2007.78. Epub Apr. 1, 2007.
Jain et al., Integration of solid-state nanopores in microfluidic networks via transfer printing of suspended membranes. Anal Chem. Apr. 16, 2013;85(8):3871-8. doi: 10.1021/ac302972c. Epub Feb. 18, 2013.
Jain, Membrane transfer process for the creation of low-noise solid state nanopore devices. Massachusetts Institute of Technology. 2011.
Jamal et al., Differentially photo-crosslinked polymers enable self-assembling microfluidics. Nature Communications. 2011;2:527.
Kang et al., Inking elastomeric stamps with micro-patterned, single layer graphene to create high-performance OFETs. Adv Mater. Aug. 16, 2011;23(31):3531-5. doi: 10.1002/adma.201101570. Epub Jul. 4, 2011.
Kasianowicz et al., Characterization of individual polynucleotide molecules using a membrane channel. Proc Natl Acad Sci U S A. Nov. 26, 1996;93(24):13770-3.
Ko et al., Ultrathin compound semiconductor on insulator layers for high-performance nanoscale transistors. Nature. Nov. 11, 2010;468(7321):286-9. doi:10.1038/nature09541.
Kong et al., Parallel gene synthesis in a microfluidic device. Nucleic Acids Res. 2007;35(8):e61. Epub Apr. 2, 2007.
Kowalczyk et al., Detection of local protein structures along DNA using solid-state nanopores. Nano Lett. Jan. 2010;10(1):324-8. doi:10.1021/n1903631m.
Kuo et al., Gateable nanofluidic interconnects for multilayered microfluidic separation systems. Anal Chem. Apr. 15, 2003;75(8):1861-7.
Lee et al., A microfluidic oligonucleotide synthesizer. Nucleic Acids Res. May 2010;38(8):2514-21. doi: 10.1093/nar/gkq092. Epub Feb. 21, 2010.
Li et al., DNA molecules and configurations in a solid-state nanopore microscope. Nat Mater. Sep. 2003;2(9):611-5. Epub Aug. 24, 2003.
Li et al., Ion-beam sculpting at nanometre length scales. Nature. Jul. 12, 2001;412(6843):166-9.

(56) References Cited

OTHER PUBLICATIONS

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Meitl et al., Transfer printing by kinetic control of adhesion to an elastomeric stamp. Nature Materials. 2006;5:33-38.

Meller et al., Voltage-driven DNA translocations through a nanopore. Phys Rev Lett. Apr. 9, 2001;86(15):3435-8.

Merchant et al., DNA translocation through graphene nanopores. Nano Lett. Aug. 11, 2010;10(8):2915-21. doi: 10.1021/nl101046t.

Mosadegh et al., Simultaneous fabrication of PDMS through-holes for three-dimensional microfluidic applications. Lab Chip. Aug. 7, 2010;10(15):1983-6. doi: 10.1039/c003590d. Epub May 26, 2010.

Naoki, Dielectric relaxation in networks of end-linked dimethylsiloxane oligomers. Polymer. 1983;24(9):1139-1144.

Novoselov et al., Two-dimensional atomic crystals. Proc Natl Acad Sci U S A. Jul. 26, 2005;102(30):10451-3. Epub Jul. 18, 2005.

Patel et al., 3D fabrication by stacking prepatterned, rigidly held membranes. J Vacuum Science Technology 2011;29(6).

Rosenstein et al., Integrated nanopore sensing platform with sub-microsecond temporal resolution. Nat Methods. Mar. 18, 2012;9(5):487-92. doi: 10.1038/nmeth.1932.

Schneider et al., DNA translocation through graphene nanopores. Nano Lett. Aug. 11, 2010;10(8):3163-7. doi: 10.1021/nl102069z.

Smeets et al., Noise in solid-state nanopores. Proc Natl Acad Sci U S A. Jan. 15, 2008;105(2):417-21. doi:10.1073/pnas.0705349105. Epub Jan. 9, 2008.

Stavis et al., Single molecule analysis of bacterial polymerase chain reaction products in submicrometer fluidic channels. Biomicrofluidics. Sep. 20, 2007;1(3):34105. doi: 10.1063/1.2789565.

Storm et al., Fabrication of solid-state nanopores with single-nanometre precision. Nat Mater. Aug. 2003;2(8):537-40.

Storm et al., Translocation of double-strand DNA through a silicon oxide nanopore. Phys Rev E Stat Nonlin Soft Matter Phys. May 2005;71(5 Pt 1):051903. Epub May 6, 2005.

Tabard-Cossa et al., Noise analysis and reduction in solid-state nanopores. Nanotechnology. 2007;18(30).

Talaga et al., Single-molecule protein unfolding in solid state nanopores. J Am Chem Soc. Jul. 8, 2009;131(26):9287-97. doi: 10.1021/ja901088b. Erratum in: J Am Chem Soc. Sep. 4, 2013;135(35):13220.

Tian et al., Accurate multiplex gene synthesis from programmable DNA microchips. Nature. Dec. 23, 2004;432(7020):1050-4.

Uram et al., Noise and bandwidth of current recordings from submicrometer pores and nanopores. ACS Nano. May 2008;2(5):857-72. doi:10.1021/nn700322m.

Van Den Heuvel et al., Molecular sorting by electrical steering of microtubules in kinesin-coated channels. Science. May 12, 2006;312(5775):910-4.

Venkatesan et al., Highly Sensitive, Mechanically Stable Nanopore Sensors for DNA Analysis. Advanced Materials. 2009;21(27):2771-2776.

Venkatesan et al., Nanopore sensors for nucleic acid analysis. Nat Nanotechnol. Sep. 18, 2011;6(10):615-24. doi: 10.1038/nnano.2011.129.

Venkatesan et al., Sensing using Nano-crystalline Surface Enhanced Al(2)O(3) Nanopore Sensors. Adv Funct Mater. Apr. 23, 2010;20(8):1266-1275. Epub Feb. 25, 2010.

Wanunu et al., Chemically modified solid-state nanopores. Nano Lett. Jun. 2007;7(6):1580-5. Epub May 16, 2007.

Wanunu et al., DNA profiling using solid-state nanopores:detection of DNA-binding molecules. Nano Lett. Oct. 2009;9(10):3498-502. doi:10.1021/nl901691v.

Wanunu et al., Electrostatic focusing of unlabelled DNA into nanoscale pores using a salt gradient. Nat Nanotechnol. Feb. 2010;5(2):160-5. doi: 10.1038/nnano.2009.379. Epub Dec. 20, 2009.

Wanunu et al., Rapid electronic detection of probe-specific microRNAs using thin nanopore sensors. Nat Nanotechnol. Nov. 2010;5(11):807-14. doi: 10.1038/nnano.2010.202. Epub Oct. 24, 2010.

Wanunu, Nanopores: A journey towards DNA sequencing. Phys Life Rev. Jun. 2012;9(2):125-58. doi: 10.1016/j.plrev.2012.05.010. Epub May 18, 2012.

Wong et al., Polymer capture by electro-osmotic flow of oppositely charged nanopores. J Chem Phys. Apr. 28, 2007;126(16):164903.

Yamada et al., Rapid quantification of disease-marker proteins using continuous-flow immunoseparation in a nanosieve fluidic device. Anal Chem. Aug. 15, 2009;81(16):7067-74. doi: 10.1021/ac901226z.

Yamamoto et al., Nanofluidic single-molecule sorting of DNA: a new concept in separation and analysis of biomolecules towards ultimate level performance. Nanotechnology. Oct. 1, 2010;21(39):395502. doi: 10.1088/0957-4484/21/39/395502. Epub Sep. 1, 2010.

\* cited by examiner

NANOFLUIDIC SORTING SYSTEM FOR GENE SYNTHESIS AND PCR REACTION PRODUCTS

RELATED APPLICATION

This application is a national stage filing under 35 U.S.C. § 371 of international application number PCT/US2013/063404, filed Oct. 4, 2013 which was published under PCT Article 21(2) in English and claims the benefit under 35 U.S.C. § 119(e) of U.S. provisional application No. 61/710,155, filed Oct. 5, 2012, each of which is incorporated by reference herein in its entirety.

FEDERALLY SPONSORED RESEARCH

This invention was made with government support under Grant No. R21 EB009180 awarded by the National Institutes of Health and under Contract No. FA8721-05-C-0002 awarded by the U.S. Air Force. The government has certain rights in the invention.

FIELD OF INVENTION

The present invention relates to microfluidic and nucleic acid nanotechnologies.

BACKGROUND OF INVENTION

Solid-state nanopores are beginning to emerge as key elements in the study of individual biomolecules such as, for example, a single nucleic acid and a single protein. Using nanopores, it is possible to directly probe individual molecules with high fidelity and high throughput. Many applications utilize solid-state nanopores including, for example, single molecule deoxyribonucleic acid (DNA) sequencing, protein unfolding, micro-ribonucleic acid (RNA) detection, label-free detection of nucleotide polymorphisms, and mapping of DNA-binding proteins such as those involved in homologous recombination. Nonetheless, current solid-state nanopore technologies are limited by, inter alia, high capacitive noise and low sampling bandwidth.

SUMMARY OF INVENTION

Rapid and inexpensive construction of synthetic genes impacts a number of applications, including basic genetic research, protein design, vaccine development and the engineering of genetic circuits with novel functions. Errors occurring during gene synthesis exponentially decrease yields with increasing gene length and obstruct inexpensive de novo synthesis of DNA molecules longer than 1-2 kilobase pairs (kbp). Consequently, synthesis of larger DNA molecules with high purity is difficult, presenting a significant impediment for biomedical research and development of the emerging field of synthetic biology.

To mitigate the effect of errors that occur during de novo DNA synthesis, longer DNA molecules are typically synthesized from shorter oligonucleotides by polymerase construction and amplification (PCA), or by other methods. Point mutations such as deletions, substitutions, and truncations are inevitable during the synthesis reaction and have to be dealt with by gel purification, cloning, and sequencing. These quality control and purification steps utilize a lot of resources and time, and limit design complexity, presenting a bottleneck for de novo DNA synthesis. Reliability is a limiting factor in gene synthesis: methods to obtain genes without errors are essential for rapid and inexpensive DNA synthesis. Thus, the present invention contemplates, in various aspects and embodiments, devices and methods that can easily interface with microfluidics for in situ quality control and high-purity selection of error-free DNA to fully enable inexpensive, high-throughput gene synthesis.

In some aspects of the invention, provided herein are devices comprising a first substrate comprising a (or one, or more than one, or at least one) microchannel, a second substrate comprising a (or one, or more than one, or at least one) microchannel, the second substrate positioned below the first substrate, and a membrane having a thickness of about 0.3 nm to about 1 µm and comprising at least one (or one, or more than one, or at least one) nanopore, the membrane positioned between the first substrate and the second substrate, wherein a single (only one) nanopore of the membrane is constructed and arranged for electrical and fluid communication between the microchannel of the first substrate and the microchannel of the second substrate.

In some embodiments, the membrane has a thickness of about 0.3 nm to about 500 nm.

In some embodiments, one side (or more than one side) of the membrane has a surface area of about 10 µm×10 µm to about 10 mm×10 mm.

In some embodiments, the membrane is a dielectric membrane. In some embodiments, the dielectric membrane is a silicon nitride (SiNx) dielectric membrane.

In some embodiments, the membranes are coated with a semiconductor (or dielectric) material. In some embodiments, the semiconductor material is at least one of alumina ($Al_2O_3$), silicon dioxide ($SiO_2$), hafnium oxide ($HfO_2$), titanium oxide ($TiO_2$), titanium nitride (TiN), graphene, hexagonal boron nitride (hBN), silicene, zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$.

In some embodiments, the microchannel of the first substrate has an inlet at a first end and an outlet at a second end. In some embodiments, the microchannel of the second substrate has an inlet at a first end and an outlet at a second end. In some embodiments, the devices further comprise a negative electrode at the inlet of the microchannel of the first substrate and a positive electrode at the outlet of the microchannel of the second substrate.

In some embodiments, the first substrate comprises 2 to 2000 microchannels. In some embodiments, the second substrate comprises 2 to 2000 microchannels.

In some embodiments, the microchannel of the first substrate is a substantially linear microchannel. In some embodiments, the microchannel of the second substrate is a substantially linear microchannel.

In some embodiments, the microchannel of the first substrate has a branched portion at one or more ends. In some embodiments, the microchannel of the second substrate has a branched portion at one or more ends. In some embodiments, the branched portion comprises 2 to 20 microchannels.

In some embodiments, the microchannel of the first substrate has a collection chamber at one or more ends. In some embodiments, the microchannel of the second substrate has a collection chamber at one or more ends.

In some embodiments, the device comprises at least one access port. In some embodiments, the first substrate comprises at least one access port. In some embodiments, the access port of the first substrate is connected to a collection chamber. In some embodiments, the second substrate comprises at least one access port. In some embodiments, the access port of the second substrate is connected to a collection chamber.

In some embodiments, a substantially horizontal axis (or a horizontal axis) of the microchannel of the first substrate is positioned at an angle of about 10° to about 90° relative to a substantially horizontal axis (or a horizontal axis) of the microchannel of the second substrate.

In some embodiments, the central portion of the microchannel of the first substrate has a width of about 100 nm to about 1 mm. In some embodiments, the central portion of the microchannel of the second substrate has a width of about 100 nm to about 1 mm.

In some embodiments, the at least one nanopore of the membrane has a diameter of about 0.2 nm to about 1 µm. In some embodiments, the at least one nanopore of the membrane has a diameter that is constructed and arranged for translocation from one microchannel to another microchannel of a single nucleic acid molecule that is 20 nucleotides to $10^6$ nucleotides in length. In some embodiments, the single nucleic acid molecule is a single-stranded nucleic acid molecule or a double-stranded nucleic acid molecule. In some embodiments, the single nucleic acid molecule is DNA or RNA. In some embodiments, the at least one nanopore of the membrane has a length of about 0.3 nm to about 1 µm.

In some embodiments, the membrane comprises 2 to 10,000 nanopores.

In some embodiments, each substrate comprises a polymer. In some embodiments, the polymer is at least one of silicone, polydimethylsiloxane (PDMS), polycarbonate, poly(methyl methacrylate), zeonax, cyclic olefin polymer (COP), polyester toner (PeT) or cellulose. In some embodiments, each substrate comprises a non-polymer. In some embodiments, the non-polymer comprises glass, silica, silicon, nitride, paper, gallium arsenide and germanium.

In some embodiments, the first substrate comprises a surface modification that enhances adhesion with the membrane. In some embodiments, the second substrate comprises a surface modification that enhances adhesion with the membrane. In some embodiments, the surface modification is at least one of a crosslinking agent, a silane group, an adhesive coating and plasma.

In some embodiments, one side of the first substrate has a surface area of about 50 µm$^2$ to about 100 mm$^2$. In some embodiments, one side of the second substrate has a surface area of about 50 µm$^2$ to about 100 mm$^2$. In some embodiments, the surface area of one side of the first substrate is about equal with the surface area of one side of the second substrate.

In some embodiments, the membrane is covalently bonded to the first substrate. In some embodiments, the membrane is covalently bonded to the second substrate.

In some embodiments, the devices further comprise an additional substrate positioned above or below the first substrate, the additional substrate comprising at least one microchannel. In some embodiments, the devices further comprise an additional substrate positioned above or below the second substrate, the additional substrate comprising at least one microchannel.

In some embodiments, the devices further comprise an additional membrane having a thickness of about 0.3 nm to about 1 µm and comprising at least one additional nanopore. In some embodiments, the devices further comprise an additional membrane having a thickness of about 0.3 nm to about 1 µm disposed between an additional substrate and the first substrate, wherein the additional membrane comprises at least one additional nanopore. In some embodiments, the devices further comprise an additional membrane having a thickness of about 0.3 nm to about 1 µm disposed between an additional substrate and the second substrate, wherein the additional membrane comprises at least one additional nanopore.

In some embodiments, the devices further comprise one or more valves.

In some embodiments, the devices are connected to a switch, amplifier, digital recorder, computer or a combination thereof.

In some aspects of the invention, provided here are arrays comprising 2 to $10^5$ devices of the invention.

In some embodiments, at least two of the devices are arranged adjacent to each other along a horizontal axis. In some embodiments, at least two of the devices are arranged adjacent to each other along a substantially vertical axis (or along a vertical axis).

In some embodiments, at least one microchannel connects the at least two devices.

In some aspects of the invention, provided herein are methods comprising providing a first substrate comprising a microchannel, wherein a membrane having a thickness of about 0.3 nm to about 1 µm and comprising at least one nanopore is disposed on a surface of the first substrate such that the at least one nanopore of the membrane contacts the microchannel of the first substrate, providing a second substrate comprising a microchannel, and contacting the membrane with the second substrate, wherein a single nanopore of the membrane provides electrical and fluid communication between the microchannel of the first substrate and the microchannel of the second substrate.

In other aspects of the invention, provided herein are methods comprising depositing a membrane having a thickness of about 0.3 nm to about 1 µm on an initial substrate, forming at least one nanopore in the membrane, contacting the membrane with a surface of a first substrate having at least one microchannel such that the at least one nanopore of the membrane contacts the at least one microchannel of the first substrate, removing the initial substrate from contact with the membrane, and contacting the membrane with a second substrate having at least one microchannel, wherein the at least one nanopore of the membrane provides electrical and fluid communication between the at least one microchannel of the first substrate and the at least one microchannel of the second substrate.

In some embodiments, the methods further comprise transferring the membrane from an initial substrate to the first substrate. In some embodiments, transferring the membrane from the initial substrate to the first substrate comprises placing the membrane in simultaneous contact with the initial substrate and the first substrate. In some embodiments, the initial substrate is a transmission electron microscopy (TEM) grid. In some embodiments, the methods further comprise detaching the membrane from the initial substrate. In some embodiments, the methods further comprise cutting a portion of the membrane prior detaching the membrane from the initial substrate.

In some embodiments, the methods further comprise bonding the membrane to the first substrate. In some embodiments, the methods further comprise bonding the membrane to the second substrate. In some embodiments, the bonding is achieved using oxygen plasma.

In some embodiments, the membrane has a thickness of about 0.3 nm to about 500 nm.

In some embodiments, the membrane is a dielectric membrane. In some embodiments, the dielectric membrane is a silicon nitride (SiNx) dielectric membrane.

In some embodiments, the membrane is coated with a semiconductor (or dielectric) material. In some embodiments, the semiconductor material is at least one of alumina ($Al_2O_3$), silicon dioxide ($SiO_2$), hafnium oxide ($HfO_2$), titanium oxide ($TiO_2$), titanium nitride (TiN), graphene, hexagonal boron nitride (hBN), silicene, zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$.

In some embodiments, the methods further comprise producing a negative mold of the first substrate comprising a microchannel. In some embodiments, the methods further comprise producing a negative mold of the second substrate comprising a microchannel. In some embodiments, the negative mold is produced using photolithography. In some embodiments, the methods further comprise adding a polymer to the mold. In some embodiments, the polymer is at least one of silicone, polydimethylsiloxane (PDMS), polycarbonate, poly(methyl methacrylate), zeonax, cyclic olefin polymer (COP), polyester toner (PeT) or cellulose. In some embodiments, the methods further comprise adding a nonpolymer to the mold. In some embodiments, the nonpolymer is glass, silica, silicon, nitride, gallium arsenide and germanium.

In some embodiments, the methods further comprise modifying the first substrate to enhance adhesion. In some embodiments, the first substrate is modified with at least one of a crosslinking agent, a silane group, an adhesive coating and plasma. In some embodiments, the methods further comprise modifying the second substrate to enhance adhesion. In some embodiments, the second substrate is modified with at least one of a crosslinking agent, a silane group, an adhesive coating and plasma.

In some embodiments, one side of the first substrate has a surface area of about 50 µm² to about 100 mm². In some embodiments, one side of the second substrate has a surface area of about 50 µm² to about 100 mm². In some embodiments, the surface area of one side of the first substrate is about equal with the surface area of one side of the second substrate.

In some embodiments, the microchannel of the first substrate has an inlet at a first end and an outlet at a second end. In some embodiments, the microchannel of the second substrate has an inlet at a first end and an outlet at a second end. In some embodiments, a negative electrode is at the inlet of the microchannel of the first substrate and a positive electrode is at the outlet of the microchannel of the second substrate.

In some embodiments, the first substrate comprises 2 to 2000 microchannels. In some embodiments, the second substrate comprises 2 to 2000 microchannels.

In some embodiments, the microchannel of the first substrate is a substantially linear microchannel. In some embodiments, the microchannel of the second substrate is a substantially linear microchannel. In some embodiments, the substantially linear microchannel of the first substrate has a branched portion at one or more ends.

In some embodiments, the substantially linear microchannel of the second substrate has a branched portion at one or more ends. In some embodiments, the branched portion comprises 2 to 20 microchannels.

In some embodiments, the microchannel of the first substrate has a collection chamber at one or more ends. In some embodiments, the microchannel of the second substrate has a collection chamber at one or more ends.

In some embodiments, the device comprises at least one access port. In some embodiments, the first substrate comprises at least one access port. In some embodiments, the access port of the first substrate is connected to a collection chamber. In some embodiments, the second substrate comprises at least one access port. In some embodiments, the access port of the second substrate is connected to a collection chamber.

In some embodiments, a substantially horizontal axis of the microchannel of the first substrate is positioned at an angle of about 10° to about 90° relative to a substantially horizontal axis of the microchannel of the second substrate.

In some embodiments, the central portion of the microchannel of the first substrate has a width of about 100 nm to about 1 mm. In some embodiments, the central portion of the microchannel of the second substrate has a width of about 100 nm to about 1 mm.

In some embodiments, the methods further comprise producing at least one nanopore of the membrane. In some embodiments, the at least one nanopore is produced using a focused ion beam (FIB), transmission electron microscopy (TEM) drilling, or nanopore etching using chemicals or plasma. In some embodiments, the FIB has a gallium ion source or a helium ion source.

In some embodiments, the at least one nanopore of the membrane has a diameter of about 0.2 nm to about 1 µm. In some embodiments, the at least one nanopore of the membrane has a diameter that provides for translocation of a single nucleic acid molecule that is 20 nucleotides to $10^6$ nucleotides in length. In some embodiments, the single nucleic acid molecule is a single-stranded nucleic acid molecule or a double-stranded nucleic acid molecule. In some embodiments, the single nucleic acid molecule is DNA or RNA. In some embodiments, the at least one nanopore of the membrane has a length of about 0.3 nm to about 1 µm.

In some embodiments, the membrane comprises 2 to 10,000 nanopores.

In some embodiments, one side of the membrane has a surface area of about 10 µm×10 µm to about 10 mm×10 mm.

In some embodiments, the methods further comprise providing an additional substrate positioned above or below the first substrate, the additional substrate comprising at least one microchannel. In some embodiments, the methods further comprise providing an additional substrate positioned above or below the second substrate, the additional substrate comprising at least one microchannel.

In some embodiments, the methods further comprise providing an additional membrane having a thickness of about 0.3 nm to about 1 µm and comprising at least one nanopore. In some embodiments, the methods further comprise providing an additional membrane having a thickness of about 0.3 nm to about 1 µm disposed between an additional substrate and the first substrate, wherein the additional membrane comprises at least one nanopore. In some embodiments, the methods further comprise providing an additional membrane having a thickness of about 0.3 nm to about 1 µm disposed between an additional substrate and the second substrate, wherein the additional membrane comprises at least one nanopore.

In some embodiments, the methods further comprise providing one or more valves positioned in the microchannel of the first substrate. In some embodiments, the methods further comprise providing one or more valves positioned in the microchannel of the second substrate.

In some embodiments, the methods further comprise connecting the first substrate to a switch, amplifier, digital recorder, computer or a combination thereof. In some embodiments, the methods further comprise connecting the second substrate to a switch, amplifier, digital recorder, computer or a combination thereof.

In some aspects of the invention, provided herein are methods comprising adding a plurality of molecules to the microchannel of the first or second substrate of a device of the invention, and applying an ionic current (or a voltage bias) across the membrane, thereby providing for translocation of a single molecule of the plurality of molecules from the microchannel of one substrate to the microchannel of another substrate through a single nanopore of the membrane.

In some embodiments, the methods further comprise recording a signal indicative of structure, composition or a combination thereof of the single molecule as the molecule translocates through the nanopore from one microchannel to another microchannel.

In some embodiments, the methods further comprise sorting the single molecule after translocation of the single molecule through the single nanopore.

In some embodiments, the sorting of the single molecule is based on the structure, the composition or the combination thereof of the single molecule.

In some embodiments, the plurality of molecules is a plurality of nucleic acid molecules. In some embodiments, the plurality of molecules is a plurality of protein molecules. In some embodiments, the plurality of nucleic acid molecules is a plurality of single-stranded DNA molecules. In some embodiments, the plurality of nucleic acid molecules is a plurality of double-stranded DNA molecules. In some embodiments, the plurality of nucleic acid molecules is a plurality of single-stranded RNA molecules. In some embodiments, the plurality of nucleic acid molecules is a plurality of double-stranded RNA molecules. In some embodiments, the plurality of nucleic acid molecules is a plurality of single-stranded DNA molecules and single-stranded RNA molecules. In some embodiments, the plurality of nucleic acid molecules is a plurality of single-stranded DNA molecules, double-stranded DNA molecules, single-stranded RNA molecules and double-stranded RNA molecules.

In some embodiments, the methods further comprise sorting each molecule of the plurality of molecules, thereby producing a sorted plurality of molecules. In some embodiments, the sorted plurality of molecules is a substantially pure plurality of molecules.

In some embodiments, the methods further comprise contacting the plurality of DNA molecules with a protein or small molecule prior to adding the plurality of DNA molecules to the device. In some embodiments, the protein is a DNA repair enzyme that binds to at least one DNA molecule of the plurality. In some embodiments, the DNA repair enzyme is a MutS mismatch-binding protein, APE 1, Endo III, Endo IV, Endo V, Endo VIII, Fpg, hOGG1, hNEIL1, T7 Endo I, T4 PDG, UDG, Afu UDG, hSMUG1 and hAAG. In some embodiments, the MutS mismatch-binding protein is from *Thermus aquaticus, Escherichia coli, Aquifex aeolicus* or *Thermotoga maritima*.

DETAILED DESCRIPTION OF INVENTION

Figure 1:
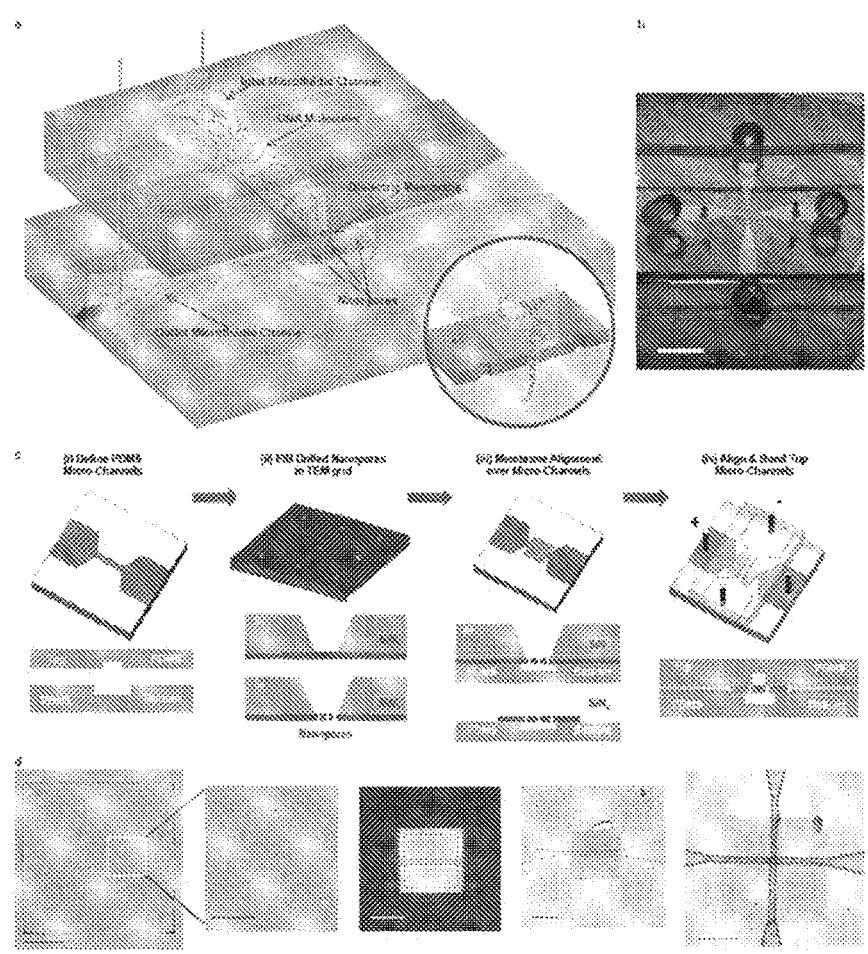
FIG. 1 depicts an example configuration of a device of the invention. (a) Schematic of device showing an ultrathin dielectric membrane flanked by two adjoining substrates that have microfluidic access channels. The inlet and outlet microchannels are connected by a single nanopore that can be used to detect single molecules of DNA (inset). (b) Optical image of device after fabrication. Scale bar of 2 mm. (c) Overview of one embodiment of the fabrication (production) process in accordance with the invention. (d) Electron and optical microscope images accompanying (c). Scale bars on these images (from left to right) are 25 µm, 8 µm, 50 µm, 50 µm and 40 µm.

Various aspects and embodiments of the invention provide, inter alia, methods and devices that integrate microfluidic systems with nanopores (e.g., microfluidics-integrated nanopore devices), providing tools for the analysis and subsequent sorting of single molecules such as, for example, single nucleic acid molecules (e.g., DNA molecules). Nanopore technology is a powerful class of technology with single molecule sensitivity and can be used to detect differences in DNA lengths (Sen et al., *Lab on a Chip*, 2012, 12(6), 1094-1101; Fologea et al., *Electrophoresis*, 2007, 28(18), 3186-319211, each of which is incorporated herein by reference), discriminate between single-stranded DNA (ssDNA) and double-stranded DNA (dsDNA) (Skinner et al., *Nano Letters*, 2009, 9(8), 2953-2960, incorporated herein by reference), and sense bound proteins (Singer et al., 2012; Kowalczyk et al., *Nano Letters*, 2010, 10(1), 324-328, each of which is incorporated herein by reference), with a direct electrical readout (Dekker et al., *Nature Nanotechnology*, 2007, 2(4), 209-215, incorporated herein by reference). Microfluidic technology offers a means to conduct cost-effective, high-throughput analyses. Thus, by combining nanopore and microfluidic technologies in a new and inventive way, the present invention provides a means to efficiently and accurately analyze and sort individual molecules based on their molecular characteristic in a cost-effective and high-throughput manner.

The invention is based, in part, on a transfer printing technique that provides for direct transfer of ultrathin membranes (e.g., ultrathin dielectric membranes) containing nanopores to microfluidic networks. Generally, these ultrathin membranes are positioned between two substrates containing microfluidic channels (also referred to herein as microchannels) such that molecular transport between the microfluidic channels is achieved by electrical manipulation of molecules through the nanopores. As a molecule translocates through a nanopore from one microchannel to another, a measurable signal indicative of structure and composition of the molecule is obtained. The devices of the invention intrinsically reduce capacitive noise by, for example, improving the signal to noise ratio (SNR), thereby providing for greater spatial and temporal resolution of individual molecules.

Devices

The devices of the invention comprise at least two substrates, each containing at least one microchannel. An ultrathin membrane comprising at least one nanopore is positioned between two substrates such that the at least one nanopore of the membrane is constructed and arranged for electrical and fluid communication between the microchannel of one substrate and the microchannel of another substrate. Thus, a single nanopore may "electrically and fluidly connect" two microchannels. One embodiment of the invention is depicted in FIG. 1a. In this Figure, one substrate is arranged above another substrate, and an ultrathin membrane comprising at least one nanopore is positioned between the two substrates.

Substrates

The devices of the invention may comprise two substrates or more than two substrates (e.g., at least two substrates). As used herein, a "substrate" refers to a surface that can be modified to contain at least one microchannel for fluid transport across or through the surface. In some embodiments, the devices may comprise 2 to 100 substrates. For example, in some embodiments, the devices may comprise 2 to 90, 2 to 80, 2 to 70, 2 to 60, 2 to 50, 2 to 40, 2 to 30, 2 to 20, 2 to 10. In some embodiments, the devices may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 88, 86, 87, 88, 89, 90, 91, 92, 93, 94, 99, 96, 97, 98, 99 or 100 substrates. In some embodiments, the devices may comprises more than 100 substrates.

The substrates may be polymeric or non-polymeric. In some embodiments, the substrates are polymeric substrates, meaning that the substrates comprises one or more polymer. In some embodiments, a substrate may comprise more than one polymer. Examples of polymers or polymeric materials that may be used in accordance with the invention include, without limitation, silicone, polydimethylsiloxane (PDMS), polycarbonate, poly(methyl methacrylate), zeonax, cyclic olefin polymer (COP), polyester toner (PeT) and cellulose. In some embodiments, the substrate is a non-polymeric substrate, meaning that the substrate comprises a material that is not a polymer. In some embodiments, a substrate may comprise more than one non-polymer or non-polymer material. Examples of non-polymers or non-polymeric materials that may be used in accordance with the invention include, without limitation, glass, silica, silicon, nitride, paper, gallium arsenide and germanium.

In some embodiments, a substrate of the invention may comprise a surface modification that enhances adhesion with the membrane or with another substrate. In some embodiments, silane-based chemistry may be used to modify the substrate (e.g., add a silane group to the substrate).

Examples of silane groups that may be added to the surface of substrates in accordance with the invention include, without limitation, 3-aminopropyl trimethoxy silane, cyclohexyltrichlorosilane and 3-mercaptopropylt-rimethoxysilane. Other examples of functional groups that may be added to the surface of the substrates in accordance with the invention include, without limitation, amine, polyethylene glycol (PEG), carboxyl, hydroxyl, methyl, phenyl, thiol and perfluoroalkyl. In some embodiments, the surface of the substrates may be modified, or further modified, with crosslinking agents. One example of a surface modification in accordance with the invention includes modification of the substrates with an amine group, followed by ethyl (dimethylaminopropyl) carbodimide-N-Hydroxysuccinimide (EDC-NHS) chemistry, followed by covalent immobilization of a biomolecule through its amine group. Another example of a surface modification in accordance with the invention includes modification with maleimide groups using silane chemistry, followed by linking with (e.g., crosslinking with) a biomolecule using a cysteine or thiol group. In some embodiments, the surface of the substrates may be modified by coating it with an adhesive coating or with gold. In some embodiments, the substrate comprises gold and is modified using thiol chemistry. In some embodiments, the surface of the substrates is modified using plasma.

A surface area of the substrates may be about 50 $\mu m^2$ to about 100 $mm^2$. For example, in some embodiments, a surface area of the substrates is about 50 $\mu m^2$ to about 100 $mm^2$, about 50 $\mu m^2$ to about 90 $mm^2$, about 50 $\mu m^2$ to about 80 $mm^2$, about 50 $\mu m^2$ to about 70 $mm^2$, about 50 $\mu m^2$ to about 60 $mm^2$, about 50 $\mu m^2$ to about 50 $mm^2$, about 50 $\mu m^2$ to about 40 $mm^2$, about 50 $\mu m^2$ to about 30 $mm^2$, about 50 $\mu m^2$ to about 20 $mm^2$, about 50 $\mu m^2$ to about 10 $mm^2$, about 50 $\mu m^2$ to about 1 $mm^2$, about 50 $\mu m^2$ to about 900 $\mu m^2$, about 50 $\mu m^2$ to about 800 $\mu m^2$, about 50 $\mu m^2$ to about 700 $\mu m^2$, about 50 $\mu m^2$ to about 600 $\mu m^2$, about 50 $\mu m^2$ to about 500 $\mu m^2$, about 50 $\mu m^2$ to about 400 $\mu m^2$, about 50 $\mu m^2$ to about 300 $\mu m^2$, about 50 $\mu m^2$ to about 200 $\mu m^2$, or about 50 $\mu m^2$ to about 100 $\mu m^2$. In some embodiments, the surface area of a substrate may be 50 $\mu m^2$, 60 $\mu m^2$, 70 $\mu m^2$, 80 $\mu m^2$, 90 $\mu m^2$, 100 $\mu m^2$, 150 $\mu m^2$, 200 $\mu m^2$, 300 $\mu m^2$, 350 $\mu m^2$, 400 $\mu m^2$, 250 $\mu m^2$, 450 $\mu m^2$, 500 $\mu m^2$, 550 $\mu m^2$, 600 $\mu m^2$, 650 $\mu m^2$, 700 $\mu m^2$, 750 $\mu m^2$, 800 $\mu m^2$, 850 $\mu m^2$, 900 $\mu m^2$, 950 $\mu m^2$, 1 $mm^2$, 2 $mm^2$, 3 $mm^2$, 4 $mm^2$, 5 $mm^2$, 6 $mm^2$, 7 $mm^2$, 8 $mm^2$, 9 $mm^2$, 10 $mm^2$, 11 $mm^2$, 12 $mm^2$, 13 $mm^2$, 14 $mm^2$, 15 $mm^2$, 16 $mm^2$, 17 $mm^2$, 18 $mm^2$, 19 $mm^2$, 20 $mm^2$, 30 $mm^2$, 31 $mm^2$, 32 $mm^2$, 33 $mm^2$, 34 $mm^2$, 35 $mm^2$, 36 $mm^2$, 37 $mm^2$, 38 $mm^2$, 39 $mm^2$, 40 $mm^2$, 41 $mm^2$, 42 $mm^2$, 43 $mm^2$, 44 $mm^2$, 45 $mm^2$, 46 $mm^2$, 47 $mm^2$, 48 $mm^2$, 49 $mm^2$, 50 $mm^2$, 51 $mm^2$, 52 $mm^2$, 53 $mm^2$, 54 $mm^2$, 55 $mm^2$, 56 $mm^2$, 57 $mm^2$, 58 $mm^2$, 59 $mm^2$, 60 $mm^2$, 61 $mm^2$, 62 $mm^2$, 63 $mm^2$, 64 $mm^2$, 65 $mm^2$, 66 $mm^2$, 67 $mm^2$, 68 $mm^2$, 69 $mm^2$, 70 $mm^2$, 71 $mm^2$, 72 $mm^2$, 73 $mm^2$, 74 $mm^2$, 75 $mm^2$, 76 $mm^2$, 77 $mm^2$, 78 $mm^2$, 79 $mm^2$, 80 $mm^2$, 81 $mm^2$, 82 $mm^2$, 83 $mm^2$, 84 $mm^2$, 85 $mm^2$, 86 $mm^2$, 87 $mm^2$, 88 $mm^2$, 89 $mm^2$, 90 $mm^2$, 91 $mm^2$, 92 $mm^2$, 93 $mm^2$, 94 $mm^2$, 95 $mm^2$, 96 $mm^2$, 97 $mm^2$, 98 $mm^2$, 99 $mm^2$ or 100 $mm^2$.

Microchannels

Figure 13:
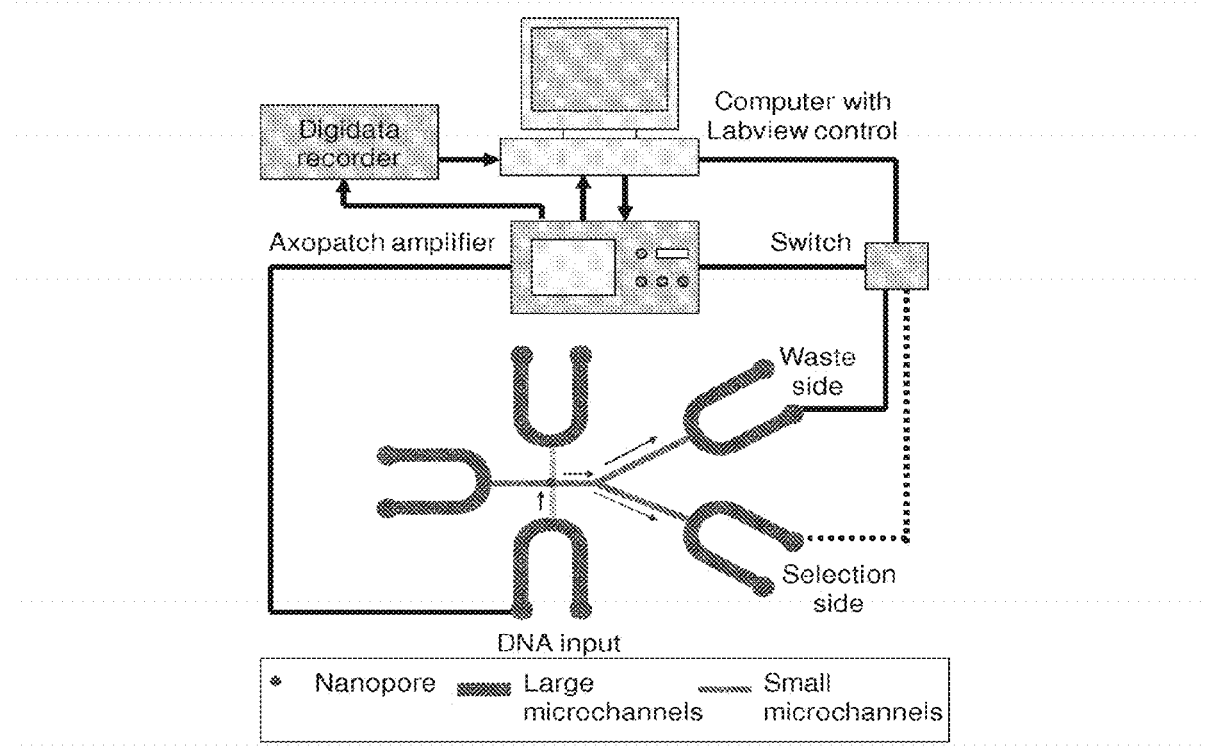
FIG. 13 shows one embodiment of the device of the invention. The device is connected to an amplifier, recorder, switch and computer.

The devices of the invention may comprise one microchannel or more than one microchannel (e.g., at least one microchannel). As used herein, a "microchannel" has at least two ends and is constructed to provide for the flow of fluid from one end to another end. Microchannels of the invention may be linear (or substantially linear). In some embodiments, the microchannels have a branched portion at one or more ends of the microchannel. One example of microchannels having branched portions is depicted in FIG. 13. The microchannels of the branched portion may be larger or smaller than the microchannel from which the branched portion is connected. In some embodiments, the branched portion of a microchannel may comprise 2 to 20 larger or smaller microchannels. For example, in some embodiments a branched portion may comprise 2, 3, 4, 5, 6, 7, 8, 9, 10, 11, 12, 13, 14, 15, 16, 17, 18, 19 or 20 microchannels. In some embodiments, a branched portion may comprises more than 20 microchannels.

The size of the microchannels of the invention may vary depending on a number of factors such as, for example, the size of the substrate, the number of microchannels of a substrate, or the size of the substrate and the number of microchannels of a substrate. The central portion of the microchannels may have a width of about 100 nm to about $10^5$ nm (0.1 mm) (or the width of the central portion of the microchannels may be, in nanometers, any number between 100 to about $10^5$). For example, in some embodiments, the central portion of the microchannels may have a width of about 100 nm to about 90000 nm, about 100 nm to about 80000 nm, about 100 nm to about 70000 nm, about 100 nm to about 60000 nm, about 100 nm to about 50000 nm, about 100 nm to about 40000 nm, about 100 nm to about 30000 nm, about 100 nm to about 20000 nm, about 100 nm to about 10000 nm, about 100 nm to about 9000 nm, about 100 nm to about 8000 nm, about 100 nm to about 7000 nm, about 100 nm to about 6000 nm, about 100 nm to about 5000 nm, about 100 nm to about 4000 nm, about 100 nm to about 3000 nm, about 100 nm to about 2000 nm, about 100 nm to about 1000 nm, or about 100 nm to about 500 nm. In some embodiments, the central portion of the microchannels may have a width of about 100 nm, 200 nm, 300 nm, 400 nm, 500 nm, 600 nm, 700 nm, 800 nm, 1000 nm, 2000 nm, 3000 nm, 4000 nm, 5000 nm, 6000 nm, 7000 nm, 8000 nm, 9000 nm, 10000 nm, 20000 nm, 30000 nm, 40000 nm, 50000 nm, 60000 nm, 70000 nm, 80000 nm, 90000 or 100000 nm. The microchannels can be any length and may be limited by the size of the substrate that comprises the microchannels.

The microchannels of the invention may have an inlet at one end of the microchannel and an outlet at the other end of the microchannel. In some embodiments, the inlet and outlets are constructed to facilitate entry and exit of fluids from the microchannel, respectively. The inlets and/or outlets may be wider than the microchannels. One example of microchannels having inlets and outlets is depicted in FIG. 1. In some embodiments, the electrodes provide for electrical manipulation of molecules through the fluid of the microchannels. In some embodiments, a negative electrode (cathode) is at the inlet of a microchannel and a positive electrode (anode) is at the outlet of the microchannel. This configuration provides for electrical manipulation of negatively charged molecules such as, for example, nucleic acids to be directed to the outlet of the microchannel.

Figure 17:
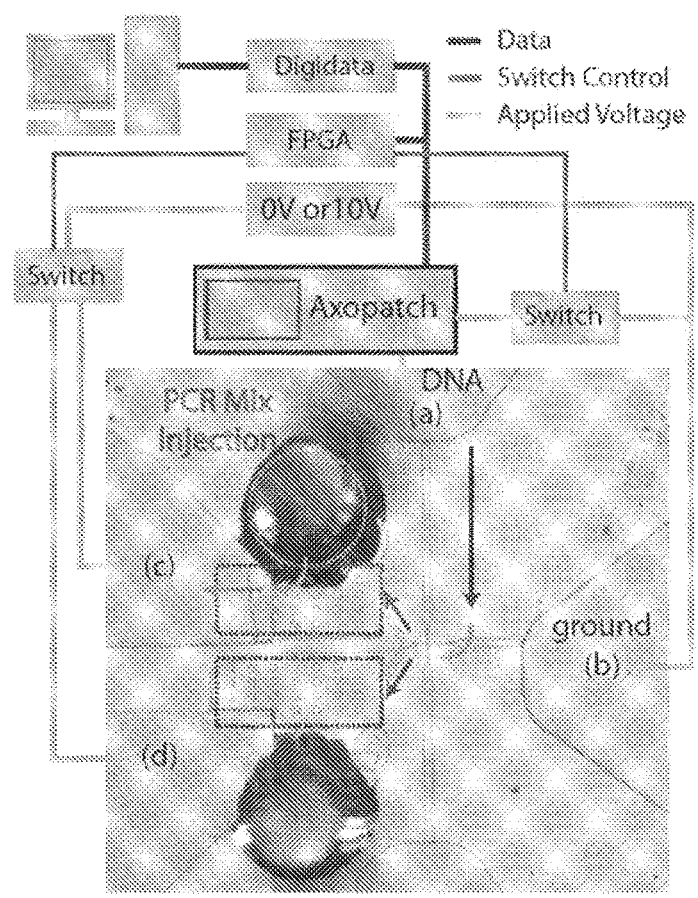
FIG. 17 shows an experimental setup for DNA sorting. Arrow in top left corner depicts flow of DNA to nanopore at the channel intersection. Top dotted box outlines collection chamber. Bottom dotted box outlines waste collection. Top circle outlines PCR injection port.

In some embodiments, the microchannels may have a collection chamber at one or more ends. For example, FIG. 17 depicts a device of the invention comprising a microchannel having a Y junction with a collection chamber at each arm of the junction (top dotted box and bottom dotted box). As used herein, a "collection chamber" refers to any reservoir for the collection of fluid.

In some embodiments, the microchannels or collection chambers may be attached to (e.g., arranged and configured to be in electric and fluid communication with) an access port (see, e.g., FIG. 17, dotted circle). Thus, a device may comprise at least one access port. As used herein, an "access port" refers to an opening in the substrate that provides for entry of fluids into the microchannels and/or collection chambers. In some embodiments, a device may comprise 1 to 20 access ports. For example, a device may comprise 1, 2, 3, 4, 5, 6, 7, 8, 9, 10, 11, 12, 13, 14, 15, 16, 17, 18, 19 or 20 access ports. In some embodiments, an inlet is considered to be an access port. An access port may be used to introduce fluids such as, for example, wash buffers and other downstream reaction mixtures (e.g., PCR reaction mixtures). Other fluids may be introduced into an access port.

In some embodiments, the microchannels are on (e.g., embedded in) the surface of the substrates. The substrates may comprises a single microchannel or 2 to 2000 microchannels (or the substrate may comprise any number of microchannels between 2 and 2000). For example, in some embodiments, the substrates may comprise 2 to 1500, 2 to 1000, 2 to 500, 2 to 250, 2 to 100, 10 to 2000, 10 to 1500, 10 to 1000, 10 to 500, 10 to 250, 10 to 200, 50 to 2000, 50 to 1500, 50 to 1000, 50 to 500, 50 to 250, 50 to 200, 100 to 2000, 100 to 1500, 100 to 1000, or 100 to 500 microchannels. In some embodiments, the substrates may comprises 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900 or 2000 microchannels. In some embodiments, the substrates may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 88, 86, 87, 88, 89, 90, 91, 92, 93, 94, 99, 96, 97, 98, 99 or 100 microchannels. The number of microchannels in a substrate may depend on factors such as, for example, the size of the microchannels, the size of the substrate, the size of the membrane, and the number of nanopores in the membrane.

In some embodiments, a substantially horizontal axis of a microchannel of one substrate is constructed and arranged at an angle of about 10° to about 90° relative to a substantially horizontal axis of a microchannel of the second substrate. For example, in some embodiments, a substantially horizontal axis of a microchannel of one substrate is positioned about 10°, about 20°, about 30°, about 40°, about 50°, about 60°, about 70°, about 80°, about 90° relative to a substantially horizontal axis of a microchannel of another substrate. One example of a microchannel of one substrate that is constructed and arranged at an angle of about 90° relative to another microchannel of another substrate is depicted in FIG. 1.

Membranes

The devices of the invention may comprises one membrane or more than one membrane (e.g., at least one membrane). In some embodiments, the devices may comprise 2 to 100 membranes. For example, in some embodiments, the devices may comprise 2 to 90, 2 to 80, 2 to 70, 2 to 60, 2 to 50, 2 to 40, 2 to 30, 2 to 20, 2 to 10, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 88, 86, 87, 88, 89, 90, 91, 92, 93, 94, 99, 96, 97, 98, 99 or 100 membranes. In some embodiments, the devices may comprise more than 100 membranes.

In some embodiments, the membranes are dielectric membranes. As used herein, a "dielectric membrane" refers to a membrane that can be polarized by an applied electric field. In some embodiments, the dielectric membranes of the invention may comprise (e.g., may be constructed from) silicon nitride (SiNx) (Dimitrov, V., et al. *Nanotechnology* 2010, 21(6): 065502, incorporated herein by reference) or another semiconductor (e.g., dielectric) material. In some embodiments, at least one surface of the membranes (e.g., membranes comprising one or more nanopores) may be coated with a semiconductor material. Examples of semiconductor materials that may be used in accordance with the invention include, without limitation, alumina ($Al_2O_3$), silicon dioxide ($SiO_2$), hafnium oxide ($HfO_2$), titanium oxide ($TiO_2$), titanium nitride (TiN), graphene, hexagonal boron nitride (hBN), silicene, zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$.

In some embodiments, at least one surface of the membranes may be coated by atomic layer deposition (ALD) (Chen, P., et al. Nano Lett. 2004, 4, 1333-1337; Venkatesan, B. M., et al. *Adv. Func. Mater.* 2010, 20, 1-10, each of which is incorporated herein by reference). In some embodiments, at least one surface of the membranes may be coated by solution-liquid-solid (SLS) growth, vapor-liquid-solid (VLS) growth (Trentlet et al. *Science*, New Series, 1995, 270(5243), 1791-1794, incorporated herein by reference), or chemical vapor deposition (CVD) (Sze, S. M. *Semiconductor devices: physics and technology*. Wiley-India, 2008, p. 384, incorporated herein by reference). In some embodiments, at least one surface of the membranes may be coated by placing flat on the membrane a piece of a two-dimensional atomic crystal by exfoliation.

The membranes of the invention may be referred to herein as "ultrathin" membranes. As used herein, an "ultrathin" membrane refers to a membrane having a thickness of about 0.3 nanometers (nm) to about 1000 nm (1 micron (µm)). Thus, in some embodiments, the membranes of the invention may have a thickness of about 0.3 nm to about 1 µm (or the thickness of the membranes may be, in nanometers, any number between 0.3 nm to about 1 µm). For example, in some embodiments, the thickness of the membranes may be about 0.3 nm to about 900 nm, about 0.3 nm to about 800 nm, about 0.3 nm to about 700 nm, about 0.3 nm to about 600 nm, about 0.3 nm to about 500 nm, about 0.3 nm to about 400 nm, about 0.3 nm to about 300 nm, about 0.3 nm to about 200 nm, about 0.3 nm to about 100 nm, about 0.3 nm to about 50 nm, about 0.3 nm to about 45 nm, about 0.3 nm to about 40 nm, about 0.3 nm to about 35 nm, about 0.3 nm to about 30 nm, about 0.3 nm to about 25 nm, about 0.3 nm to about 20 nm, about 0.3 nm to about 15 nm, about 0.3 nm to about 10 nm, about 0.3 nm to about 5 nm, about 0.3 nm to about 2.5 nm, or about 0.3 nm to about 1 nm. In some embodiments, the thickness of the membranes may be 0.3 nm, 0.3 nm, 0.4 nm, 0.5 nm, 0.6 nm, 0.7 nm, 0.8 nm, 0.9 nm, 1.0 nm, 1.5 nm, 2 nm, 2.5 nm, 3.0 nm, 3.5 nm, 4.0 nm, 4.5 nm, 5.0 nm, 5.5 nm, 6.0 nm, 6.5 nm, 7.0 nm, 7.5 nm, 8.0 nm, 8.5 nm, 9.0 nm, 9.5 nm, 10.0 nm, 10.5 nm, 11.0 nm, 11.5 nm, 12.0 nm, 12.5 nm, 13.0 nm, 13.5 nm, 14.0 nm, 14.5 nm, 15.0 nm, 15.5 nm, 16.0 nm, 16.5 nm, 17.0 nm, 17.5 nm, 18.0 nm, 18.5 nm, 19.0 nm, 19.5 nm, 20.0 nm, 20.5 nm, 21.0 nm, 21.5 nm, 22.0 nm, 22.5 nm, 23.0 nm, 23.5 nm, 24.0 nm, 24.5 nm, 25.0 nm, 25.5 nm, 26.0 nm, 26.5 nm, 27.0 nm, 27.5 nm, 28.0 nm, 28.5 nm, 29.0 nm, 29.5 nm, 30.0 nm, 30.5 nm, 31.0 nm, 31.5 nm, 32.0 nm, 32.5 nm, 33.0 nm, 33.5 nm, 34.0 nm, 34.5 nm, 35.0 nm, 35.5 nm, 36.0 nm, 36.5 nm, 37.0 nm, 37.5 nm, 38.0 nm, 38.5 nm, 39.0 nm, 39.5 nm, 40.0 nm, 40.5 nm, 41.0 nm, 41.5 nm, 42.0 nm, 42.5 nm, 43.0 nm, 43.5 nm, 44.0 nm, 44.5 nm, 45.0 nm, 45.5 nm, 46.0 nm, 46.5 nm, 47.0 nm, 47.5 nm, 48.0 nm, 48.5 nm, 49.0 nm, 49.5 nm, 50.0 nm, 50.5 nm, 51.0 nm, 51.5 nm, 52.0 nm, 52.5 nm, 53.0 nm, 53.5 nm, 54.0 nm, 54.5 nm, 55.0 nm, 55.5 nm, 56.0 nm, 56.5 nm, 57.0 nm, 57.5 nm, 58.0 nm, 58.5 nm, 59.0 nm, 59.5 nm, 60.0 nm, 60.5 nm, 61.0 nm, 61.5 nm, 62.0 nm, 62.5 nm, 63.0 nm, 63.5 nm, 64.0 nm, 64.5 nm, 65.0 nm, 65.5 nm, 66.0 nm, 66.5 nm, 67.0 nm, 67.5 nm, 68.0 nm, 68.5 nm, 69.0 nm, 69.5 nm, 70.0 nm, 70.5 nm, 71.0 nm, 71.5 nm, 72.0 nm, 72.5 nm, 73.0 nm, 73.5 nm, 74.0 nm, 74.5 nm, 75.0 nm, 75.5 nm, 76.0 nm, 76.5 nm, 77.0 nm, 77.5 nm, 78.0 nm, 78.5 nm, 79.0 nm, 79.5 nm, 80.0 nm, 80.5 nm, 81.0 nm, 81.5 nm, 82.0 nm, 82.5 nm, 83.0 nm, 83.5 nm, 84.0 nm, 84.5 nm, 85.0 nm, 85.5 nm, 86.0 nm, 86.5 nm, 87.0 nm, 87.5 nm, 88.0 nm, 88.5 nm, 89.0 nm, 89.5 nm, 90.0 nm, 90.5 nm, 91.0 nm, 91.5 nm, 92.0 nm, 92.5 nm, 93.0 nm, 93.5 nm, 94.0 nm, 94.5 nm, 95.0 nm, 95.5 nm, 96.0 nm, 96.5 nm, 97.0 nm, 97.5 nm, 98.0 nm, 98.5 nm, 99.0 nm, 99.5 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm.

In some embodiments, one side of a membrane may have a surface area of about 10 μm×10 μm to about 10000 μm×10000 μm (10 mm×10 mm) (or the surface area of one side of a membrane may be, in micrometers squared (μm$^2$), any number between 10 and 10000). For example, in some embodiments, the surface area of one side of the membrane may be about 10 μm$^2$ to about 9000 μm$^2$, about 10 μm$^2$ to about 8000 μm$^2$, about 10 μm$^2$ to about 7000 μm$^2$, about 10 μm$^2$ to about 6000 μm$^2$, about 10 μm$^2$ to about 5000 μm$^2$, about 10 μm$^2$ to about 4000 μm$^2$, about 10 μm$^2$ to about 3000 μm$^2$, about 10 μm$^2$ to about 2000 μm$^2$, about 10 μm$^2$ to about 1000 μm$^2$, about 10 μm$^2$ to about 900 μm$^2$, about 10 μm$^2$ to about 800 μm$^2$, about 10 μm$^2$ to about 700 μm$^2$, about 10 μm$^2$ to about 600 μm$^2$, about 10 μm$^2$ to about 500 μm$^2$, about 10 μm$^2$ to about 400 μm$^2$, about 10 μm$^2$ to about 300 μm$^2$, about 10 μm$^2$ to about 200 μm$^2$, about 10 μm$^2$ to about 100 μm$^2$. In some embodiments, the surface area of one side of the membrane may be 10 μm$^2$, 20 μm$^2$, 30 μm$^2$, 40 μm$^2$, 50 μm$^2$, 60 μm$^2$, 70 μm$^2$, 80 μm$^2$, 90 μm$^2$, 100 μm$^2$, 200 μm$^2$, 300 μm$^2$, 400 μm$^2$, 500 μm$^2$, 600 μm$^2$, 700 μm$^2$, 800 μm$^2$, 900 μm$^2$, 1000 μm$^2$, 2000 μm$^2$, 3000 μm$^2$, 4000 μm$^2$, 5000 μm$^2$, 6000 μm$^2$, 7000 μm$^2$, 8000 μm$^2$, 9000 μm$^2$ or 10000 μm$^2$. The surface areas of the membranes may depend on factors such as, for example, the size of the surface area of the substrate, the number and size of microchannels of a substrate, and the number of nanopores of the membrane.

In some embodiments, the membranes may be covalently bonded to the substrates. In some embodiments, the membranes may be non-covalently bonded to the substrates.

Nanopores

The membranes of the invention may have one nanopore or more than one nanopore (e.g., at least one nanopore). As used herein, a "nanopore" refers to a hole that is equal to or less than 1 micron in diameter. In some embodiments, the membranes may comprise 2 to 10000 nanopores (or the membranes may comprise nanopores of any number between 2 and 10000). For example, in some embodiments, the membranes may comprise 2 to 9000, 2 to 8000, 2 to 7000, 2 to 6000, 2 to 5000, 2 to 4000, 2 to 3,000, 2 to 2,000, 2 to 1000, 2 to 900, 2 to 800, 2 to 700, 2 to 600, 2 to 500, 2 to 400, 2 to 300, 2 to 200, 2 to 100, 2 to 90, 2 to 80, 2 to 70, 2 to 60, 2 to 50, 2 to 40, 2 to 30, 2 to 20 or 2 to 10 nanopores. In some embodiments, the membranes may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 88, 86, 87, 88, 89, 90, 91, 92, 93, 94, 99, 96, 97, 98, 99, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500 or 10,000 nanopores. In some embodiments, the membranes may comprise more than 10000 nanopores. The number of nanopores in a membrane may depend on factors such as, for example, the size of the nanopores, the size of the membrane, and the number of microchannels of substrates, and the size of the microchannels of substrates of the devices.

The diameter and length of the nanopores of the invention may vary. The diameter of the nanopores may be about 0.2 nm to about 1000 nm (1 μm) (or the diameter of the nanopore, in nanometers, may be any number between 0.2 and 1000). For example, in some embodiments, the diameter of the nanopores in accordance with the invention may be about 0.2 nm to about 900 nm, about 0.2 nm to about 800 nm, about 0.2 nm to about 700 nm, about 0.2 nm to about 600 nm, about 0.2 nm to about 500 nm, about 0.2 nm to about 400 nm, about 0.2 nm to about 300 nm, about 0.2 nm to about 200 nm, about 0.2 nm to about 100 nm, about 0.2 nm to about 90 nm, about 0.2 nm to about 80 nm, about 0.2 nm to about 70 nm, about 0.2 nm to about 60 nm, about 0.2 nm to about 50 nm, about 0.2 nm to about 40 nm, about 0.2 nm to about 30 nm, about 0.2 nm to about 20 nm, about 0.2 nm to about 10 nm, about 0.2 nm to about 5 nm, or about 0.2 nm to about 1 nm. In some embodiments, the diameter of the nanopores may be 0.2 nm, 0.3 nm, 0.4 nm, 0.5 nm, 0.6 nm, 0.7 nm, 0.8 nm, 0.9 nm, 1.0 nm, 1.5 nm, 2 nm, 2.5 nm, 3.0 nm, 3.5 nm, 4.0 nm, 4.5 nm, 5.0 nm, 5.5 nm, 6.0 nm, 6.5 nm, 7.0 nm, 7.5 nm, 8.0 nm, 8.5 nm, 9.0 nm, 9.5 nm, 10.0 nm, 10.5 nm, 11.0 nm, 11.5 nm, 12.0 nm, 12.5 nm, 13.0 nm, 13.5 nm, 14.0 nm, 14.5 nm, 15.0 nm, 15.5 nm, 16.0 nm, 16.5 nm, 17.0 nm, 17.5 nm, 18.0 nm, 18.5 nm, 19.0 nm, 19.5 nm, 20.0 nm, 20.5 nm, 21.0 nm, 21.5 nm, 22.0 nm, 22.5 nm, 23.0 nm, 23.5 nm, 24.0 nm, 24.5 nm, 25.0 nm, 25.5 nm, 26.0 nm, 26.5 nm, 27.0 nm, 27.5 nm, 28.0 nm, 28.5 nm, 29.0 nm, 29.5 nm, 30.0 nm, 30.5 nm, 31.0 nm, 31.5 nm, 32.0 nm, 32.5 nm, 33.0 nm, 33.5 nm, 34.0 nm, 34.5 nm, 35.0 nm, 35.5 nm, 36.0 nm, 36.5 nm, 37.0 nm, 37.5 nm, 38.0 nm, 38.5 nm, 39.0 nm, 39.5 nm, 40.0 nm, 40.5 nm, 41.0 nm, 41.5 nm, 42.0 nm, 42.5 nm, 43.0 nm, 43.5 nm, 44.0 nm, 44.5 nm, 45.0 nm, 45.5 nm, 46.0 nm, 46.5 nm, 47.0 nm, 47.5 nm, 48.0 nm, 48.5 nm, 49.0 nm, 49.5 nm, 50.0 nm, 50.5 nm, 51.0 nm, 51.5 nm, 52.0 nm, 52.5 nm, 53.0 nm, 53.5 nm, 54.0 nm, 54.5 nm, 55.0 nm, 55.5 nm, 56.0 nm, 56.5 nm, 57.0 nm, 57.5 nm, 58.0 nm, 58.5 nm, 59.0 nm, 59.5 nm, 60.0 nm, 60.5 nm, 61.0 nm, 61.5 nm, 62.0 nm, 62.5 nm, 63.0 nm, 63.5 nm, 64.0 nm, 64.5 nm, 65.0 nm, 65.5 nm, 66.0 nm, 66.5 nm, 67.0 nm, 67.5 nm, 68.0 nm, 68.5 nm, 69.0 nm, 69.5 nm, 70.0 nm, 70.5 nm, 71.0 nm, 71.5 nm, 72.0 nm, 72.5 nm, 73.0 nm, 73.5 nm, 74.0 nm, 74.5 nm, 75.0 nm, 75.5 nm, 76.0 nm, 76.5 nm, 77.0 nm, 77.5 nm, 78.0 nm, 78.5 nm, 79.0 nm, 79.5 nm, 80.0 nm, 80.5 nm, 81.0 nm, 81.5 nm, 82.0 nm, 82.5 nm, 83.0 nm, 83.5 nm, 84.0 nm, 84.5 nm, 85.0 nm, 85.5 nm, 86.0 nm, 86.5 nm, 87.0 nm, 87.5 nm, 88.0 nm, 88.5 nm, 89.0 nm, 89.5 nm, 90.0 nm, 90.5 nm, 91.0 nm, 91.5 nm, 92.0 nm, 92.5 nm, 93.0 nm, 93.5 nm, 94.0 nm, 94.5 nm, 95.0 nm, 95.5 nm, 96.0 nm, 96.5 nm, 97.0 nm, 97.5 nm, 98.0 nm, 98.5 nm, 99.0 nm, 99.5 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm.

In some embodiments, the nanopores are of a length that is sufficient to traverse the thickness of the membrane. In some embodiments, the length of the nanopores may be about 0.3 nm to about 1 µm (or the length of the nanopore, in nanometers, may be any number between 0.3 and 1000). For example, in some embodiments, the length of the nanopores may be about 0.3 nm to about 900 nm, about 0.3 nm to about 800 nm, about 0.3 nm to about 700 nm, about 0.3 nm to about 600 nm, about 0.3 nm to about 500 nm, about 0.3 nm to about 400 nm, about 0.3 nm to about 300 nm, about 0.3 nm to about 300 nm, about 0.3 nm to about 200 nm, about 0.3 nm to about 100 nm, about 0.3 nm to about 50 nm, about 0.3 nm to about 45 nm, about 0.3 nm to about 40 nm, about 0.3 nm to about 35 nm, about 0.3 nm to about 30 nm, about 0.3 nm to about 25 nm, about 0.3 nm to about 20 nm, about 0.3 nm to about 15 nm, about 0.3 nm to about 10 nm, about 0.3 nm to about 5 nm, about 0.3 nm to about 2.5 nm, or about 0.3 nm to about 1 nm. In some embodiments, the length of the nanopores may be 0.3 nm, 0.4 nm, 0.5 nm, 0.6 nm, 0.7 nm, 0.8 nm, 0.9 nm, 1.0 nm, 1.5 nm, 2 nm, 2.5 nm, 3.0 nm, 3.5 nm, 4.0 nm, 4.5 nm, 5.0 nm, 5.5 nm, 6.0 nm, 6.5 nm, 7.0 nm, 7.5 nm, 8.0 nm, 8.5 nm, 9.0 nm, 9.5 nm, 10.0 nm, 10.5 nm, 11.0 nm, 11.5 nm, 12.0 nm, 12.5 nm, 13.0 nm, 13.5 nm, 14.0 nm, 14.5 nm, 15.0 nm, 15.5 nm, 16.0 nm, 16.5 nm, 17.0 nm, 17.5 nm, 18.0 nm, 18.5 nm, 19.0 nm, 19.5 nm, 20.0 nm, 20.5 nm, 21.0 nm, 21.5 nm, 22.0 nm, 22.5 nm, 23.0 nm, 23.5 nm, 24.0 nm, 24.5 nm, 25.0 nm, 25.5 nm, 26.0 nm, 26.5 nm, 27.0 nm, 27.5 nm, 28.0 nm, 28.5 nm, 29.0 nm, 29.5 nm, 30.0 nm, 30.5 nm, 31.0 nm, 31.5 nm, 32.0 nm, 32.5 nm, 33.0 nm, 33.5 nm, 34.0 nm, 34.5 nm, 35.0 nm, 35.5 nm, 36.0 nm, 36.5 nm, 37.0 nm, 37.5 nm, 38.0 nm, 38.5 nm, 39.0 nm, 39.5 nm, 40.0 nm, 40.5 nm, 41.0 nm, 41.5 nm, 42.0 nm, 42.5 nm, 43.0 nm, 43.5 nm, 44.0 nm, 44.5 nm, 45.0 nm, 45.5 nm, 46.0 nm, 46.5 nm, 47.0 nm, 47.5 nm, 48.0 nm, 48.5 nm, 49.0 nm, 49.5 nm, 50.0 nm, 50.5 nm, 51.0 nm, 51.5 nm, 52.0 nm, 52.5 nm, 53.0 nm, 53.5 nm, 54.0 nm, 54.5 nm, 55.0 nm, 55.5 nm, 56.0 nm, 56.5 nm, 57.0 nm, 57.5 nm, 58.0 nm, 58.5 nm, 59.0 nm, 59.5 nm, 60.0 nm, 60.5 nm, 61.0 nm, 61.5 nm, 62.0 nm, 62.5 nm, 63.0 nm, 63.5 nm, 64.0 nm, 64.5 nm, 65.0 nm, 65.5 nm, 66.0 nm, 66.5 nm, 67.0 nm, 67.5 nm, 68.0 nm, 68.5 nm, 69.0 nm, 69.5 nm, 70.0 nm, 70.5 nm, 71.0 nm, 71.5 nm, 72.0 nm, 72.5 nm, 73.0 nm, 73.5 nm, 74.0 nm, 74.5 nm, 75.0 nm, 75.5 nm, 76.0 nm, 76.5 nm, 77.0 nm, 77.5 nm, 78.0 nm, 78.5 nm, 79.0 nm, 79.5 nm, 80.0 nm, 80.5 nm, 81.0 nm, 81.5 nm, 82.0 nm, 82.5 nm, 83.0 nm, 83.5 nm, 84.0 nm, 84.5 nm, 85.0 nm, 85.5 nm, 86.0 nm, 86.5 nm, 87.0 nm, 87.5 nm, 88.0 nm, 88.5 nm, 89.0 nm, 89.5 nm, 90.0 nm, 90.5 nm, 91.0 nm, 91.5 nm, 92.0 nm, 92.5 nm, 93.0 nm, 93.5 nm, 94.0 nm, 94.5 nm, 95.0 nm, 95.5 nm, 96.0 nm, 96.5 nm, 97.0 nm, 97.5 nm, 98.0 nm, 98.5 nm, 99.0 nm, 99.5 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm.

In some embodiments, the diameter and the length of the nanopores are constructed and arranged for translocation from one microchannel to another microchannel of a single nucleic acid molecule that is 20 nucleotides to $10^5$ nucleotides in length (or the length of a single nucleic acid molecule may be, in nucleotides, any number between 20 and $10^5$). For example, in some embodiments, the nucleic acid molecule is 20 to 100000, 20 to 10000, 20 to 1000, or 20 to 100 nucleotides in length. In some embodiments, the nucleic acid molecule is 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000, 40000, 45000, 50000, 55000, 60000, 65000, 70000, 75000, 80000, 85000, 90000, 95000 or 100000 nucleotides. In some embodiments, the nucleic acid may be single-stranded. In some embodiments, the nucleic acid may be double-stranded. In some embodiments the single-stranded nucleic acid may be DNA. In some embodiments the single-stranded nucleic acid may be RNA. In some embodiments the double-stranded nucleic acid may be DNA. In some embodiments the double-stranded nucleic acid may be RNA. In some embodiments the double-stranded nucleic acid may be a combination of DNA and RNA, such as one strand of DNA and one strand of RNA. In some embodiments, the nucleic acid may be naturally occurring. In some embodiments, the nucleic acid may be synthetic.

Valves and Switches

The devices of the invention may comprise one valve or more than one valve (e.g., at least one valve). As used herein, a "valve" refers to a device that regulates, directs or controls the flow of a fluid by opening, closing, or partially obstructing a microchannel. Any of a number of valves suitable for use in a device such as that described herein can be selected by those of ordinary skill in the art including, without limitation, those described in U.S. Pat. No. 6,767,194, "Valves and Pumps for Microfluidic Systems and Methods for Making Microfluidic Systems", and U.S. Pat. No. 6,793,753, "Method of Making a Microfabricated Elastomeric Valve," each of which is incorporated herein by reference. In some embodiments, the valves may be fabricated using simple lithographic procedures.

Amplifiers and Recorders

The devices of the invention may be used in conjunction with bioanalytical systems, instruments, equipment and software. In some embodiments, the devices are used in conjunction with conventional patch clamp systems useful for microelectrode recording techniques. For example, in some embodiments, the devices are connected to an amplifier (e.g., Axon Axopatch Capacitor Feedback Patch Clamp Amplifier, Molecular Devices). Amplifiers may be used in accordance with the invention for single-channel recordings (e.g., as a molecule translocates through a nanopore) (see Wanunu M. *Physics of Life Reviews*, 2012, 9, 125-158, incorporated herein by reference) to improve signal-to-noise ratios (Rosenstein et al. *Nature Methods*, 2012, 9, 487-492, incorporated herein by reference). In some embodiments, the devices are connected to a data acquisition system for electrophysiology recordings (e.g., Axon Digidata Data Acquisition System and associated software, Molecular Devices). Any of a number of bioanalytical systems suitable for use in devices such as those described herein can be selected by those of ordinary skill in the art.

Arrays

The devices of the invention typically comprise two substrates, each containing at least one microchannel and each separated by an ultrathin membrane. Also contemplated herein are complex, microfluidic-nanopore arrays (e.g., three-dimensional arrays) comprising more than two substrates. For example, multiple substrates and membranes of the invention may be configured and arranged such that molecules can be moved by electrical manipulation through nanopores from microchannels of a first substrate, to microchannels a second adjacent substrate, to microchannels a third substrate adjacent to the second substrate, and so on. Two or more substrates may be arranged adjacent to each other along a horizontal axis, or they may be stacked on top of each other along a substantially vertical axis. In some embodiments, an array comprises a combination of the foregoing arrangements. Two substrates are considered "adjacent" to each other when one surface of one substrate is on contact with one surface of another substrate.

For substrates that are stacked on top of each other (e.g., adjacent along a substantially vertical axis), an ultrathin membrane containing nanopore(s) may be configured and arranged between the two substrates such that a single nanopore electrically and fluidly connects microchannels in adjacent substrates, providing for translocation of a molecule between adjacent substrates. Thus, it is contemplated that a three-dimensional array may comprise more than one ultrathin membrane. Alternatively, an array in accordance with the invention may comprise multiple devices of the invention (e.g., devices comprising at least two substrates, each substrate separated by an ultrathin membrane containing nanopore(s)) configured and arranged adjacent to each other along a horizontal axis, much like a "lab-on-chip" configuration.

In some embodiments, the arrays may comprise 2 to $10^5$ substrates and/or membranes. For example, an array in accordance with the invention may comprise 2, 3, 4, 5, 6, 7, 8, 9, 10, 11, 12, 13, 14, 15, 16, 17, 18, 19, 20, 35, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 20000, 30000, 40000, 50000, 60000, 70000, 80000, 90000 or 100000 substrates and/or membranes. The foregoing arrangements and configurations are examples of the many array arrangements and configurations contemplated herein.

Methods of Production/Fabrication

Provided herein are methods of producing (also referred to herein as fabrication) any of the devices of the invention. A detailed description of how some of the devices are fabricated is provided herein in the Figures and Examples.

FIG. 1(c) depicts one embodiment of the production process in accordance with the invention. First, microchannels are defined in polydimethylsiloxane (PDMS) using soft lithography (FIG. 1(c)(i)). TEM grids are then patterned with a focused ion beam (FIB), opening nanopores with diameters of, for example, about 25 nm (FIG. 1(c)(ii)). Next, the patterned grid and PDMS microchannel are treated with oxygen plasma, spatially registered over one another using a custom-built aligner, and contacted. The TEM grid is then peeled away, leaving behind a patterned ultrathin dielectric membrane that is covalently bonded over a microfluidic channel (FIG. 1(c)(iii)). Finally, another identical PDMS microchannel (rotated 90°) is plasma treated, positioned over the membrane in an identical fashion and brought into conformal contact such that a single nanopore electrically and fluidly connects the two microfluidic channels. Ag/AgCl electrodes are then inserted into the microchannel access ports (e.g., inlets/outlets) (FIG. 1(c)(iv)).

Membranes of the invention may be constructed by utilizing transfer printing techniques (Meitl, M. A., et al. *Nature Mater.* 2006, 5, 33-38; Ahn, J. H., et al. *Science* 2006, 314, 1754-1757, each of which is incorporated herein by reference) that permit functional registration of nanopores of ultrathin membranes (e.g., dielectric membranes) between microchannels. In some embodiments, a transfer printing technique according to the invention is used to construct devices comprising ultrathin membranes of a thickness of about 0.3 nm to about 1 μm. Thus, in some embodiments, a transfer printing technique may be used to construct ultrathin membranes having a thickness of about 0.3 nm to about 900 nm, about 0.3 nm to about 800 nm, about 0.3 nm to about 700 nm, about 0.3 nm to about 600 nm, about 0.3 nm to about 500 nm, about 0.3 nm to about 400 nm, about 0.3 nm to about 300 nm, about 0.3 nm to about 200 nm, about 0.3 nm to about 100 nm, about 0.3 nm to about 50 nm, about 0.3 nm to about 45 nm, about 0.3 nm to about 40 nm, about 0.3 nm to about 35 nm, about 0.3 nm to about 30 nm, about 0.3 nm to about 25 nm, about 0.3 nm to about 20 nm, about 0.3 nm to about 15 nm, about 0.3 nm to about 10 nm, about 0.3 nm to about 5 nm, about 0.3 nm to about 2.5 nm, or about 0.3 nm to about 1 nm. In some embodiments, the thickness of the membranes may be 0.3 nm, 0.3 nm, 0.4 nm, 0.5 nm, 0.6 nm, 0.7 nm, 0.8 nm, 0.9 nm, 1.0 nm, 1.5 nm, 2 nm, 2.5 nm, 3.0 nm, 3.5 nm, 4.0 nm, 4.5 nm, 5.0 nm, 5.5 nm, 6.0 nm, 6.5 nm, 7.0 nm, 7.5 nm, 8.0 nm, 8.5 nm, 9.0 nm, 9.5 nm, 10.0 nm, 10.5 nm, 11.0 nm, 11.5 nm, 12.0 nm, 12.5 nm, 13.0 nm, 13.5 nm, 14.0 nm, 14.5 nm, 15.0 nm, 15.5 nm, 16.0 nm, 16.5 nm, 17.0 nm, 17.5 nm, 18.0 nm, 18.5 nm, 19.0 nm, 19.5 nm, 20.0 nm, 20.5 nm, 21.0 nm, 21.5 nm, 22.0 nm, 22.5 nm, 23.0 nm, 23.5 nm, 24.0 nm, 24.5 nm, 25.0 nm, 25.5 nm, 26.0 nm, 26.5 nm, 27.0 nm, 27.5 nm, 28.0 nm, 28.5 nm, 29.0 nm, 29.5 nm, 30.0 nm, 30.5 nm, 31.0 nm, 31.5 nm, 32.0 nm, 32.5 nm, 33.0 nm, 33.5 nm, 34.0 nm, 34.5 nm, 35.0 nm, 35.5 nm, 36.0 nm, 36.5 nm, 37.0 nm, 37.5 nm, 38.0 nm, 38.5 nm, 39.0 nm, 39.5 nm, 40.0 nm, 40.5 nm, 41.0 nm, 41.5 nm, 42.0 nm, 42.5 nm, 43.0 nm, 43.5 nm, 44.0 nm, 44.5 nm, 45.0 nm, 45.5 nm, 46.0 nm, 46.5 nm, 47.0 nm, 47.5 nm, 48.0 nm, 48.5 nm, 49.0 nm, 49.5 nm, 50.0 nm, 50.5 nm, 51.0 nm, 51.5 nm, 52.0 nm, 52.5 nm, 53.0 nm, 53.5 nm, 54.0 nm, 54.5 nm, 55.0 nm, 55.5 nm, 56.0 nm, 56.5 nm, 57.0 nm, 57.5 nm, 58.0 nm, 58.5 nm, 59.0 nm, 59.5 nm, 60.0 nm, 60.5 nm, 61.0 nm, 61.5 nm, 62.0 nm, 62.5 nm, 63.0 nm, 63.5 nm, 64.0 nm, 64.5 nm, 65.0 nm, 65.5 nm, 66.0 nm, 66.5 nm, 67.0 nm, 67.5 nm, 68.0 nm, 68.5 nm, 69.0 nm, 69.5 nm, 70.0 nm, 70.5 nm, 71.0 nm, 71.5 nm, 72.0 nm, 72.5 nm, 73.0 nm, 73.5 nm, 74.0 nm, 74.5 nm, 75.0 nm, 75.5 nm, 76.0 nm, 76.5 nm, 77.0 nm, 77.5 nm, 78.0 nm, 78.5 nm, 79.0 nm, 79.5 nm, 80.0 nm, 80.5 nm, 81.0 nm, 81.5 nm, 82.0 nm, 82.5 nm, 83.0 nm, 83.5 nm, 84.0 nm, 84.5 nm, 85.0 nm, 85.5 nm, 86.0 nm, 86.5 nm, 87.0 nm, 87.5 nm, 88.0 nm, 88.5 nm, 89.0 nm, 89.5 nm, 90.0 nm, 90.5 nm, 91.0 nm, 91.5 nm, 92.0 nm, 92.5 nm, 93.0 nm, 93.5 nm, 94.0 nm, 94.5 nm, 95.0 nm, 95.5 nm, 96.0 nm, 96.5 nm, 97.0 nm, 97.5 nm, 98.0 nm, 98.5 nm, 99.0 nm, 99.5 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm.

An ultrathin membrane in accordance with the invention may be any shape. For example, a surface of the membrane may be square, rectangular, triangular, circular, rhomboid or in the shape of a cross (e.g., "+" or "×").

Cuts around the membrane (e.g., at least one cut along the edge of the membrane) may be made to provide for membrane transfer to a receiving substrate (e.g., PDMS substrate) (Mosadegh, B., et al. *Lab On A Chip* 2010, 10, 1983-1986; Patel, A. A., et al. *J. Vac. Sci. Tech.* B 2011, 29, 06F402, each of which is incorporated herein by reference) (see e.g., FIG. 1(d), membrane of far right panel). The cuts may be made using, for example, a focused ion beam drilling tool. This tool uses high energy ions to bombard a surface and selectively remove membrane material. The number and location of the cuts may vary. In some embodiments, where the surface area of a membrane is square, cuts may be made on each of the four edges of the square. In some embodiments, 1, 2, 3, 4, 5, 6, 7, 8, 9 or 10 cuts are made in a membrane. In some embodiments, more than 10 cuts are made in a membrane.

Nanopores of the invention may be constructed by a variety of means. For example, in some embodiments, nanopores may be constructed by drilling a nanometer-scale hole in an ultrathin membrane using ion beam (Li, J., et al. *Nature* 2001, 412, 166-169, incorporated herein by reference) or electron beam irradiation (Storm, A. J., et al. *Nature*

*Mater.* 2003, 2, 537-540, incorporated herein by reference). In some embodiments, the pitch between nanopores is set at a predetermined value. As used herein, "pitch" may refer to the distance between neighboring nanopores. In some embodiments, the pitch between the nanopores may be set to equal the microchannel width. This may provide for a high probability that a single pore in the array is registered between two microchannels.

The nanopores may be further modified by, for example, atomic layer deposition (ALD), solution-liquid-solid (SLS) growth, vapor-liquid-solid (VLS) growth, or chemical vapor deposition (CVD). In some embodiments, at least one of alumina ($Al_2O_3$), silicon dioxide ($SiO_2$), hafnium oxide ($HfO_2$), titanium oxide ($TiO_2$), titanium nitride (TiN), graphene, hexagonal boron nitride (hBN), silicene, zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$ may be deposited on membranes than contain nanopores. It is to be understood that any of the foregoing materials, or any combination of two or more of the foregoing materials, may be deposited on the membranes of the invention.

Methods of Use

While nanopore technology offers several advantages—including small sample requirement, electrical readout, single molecule sensitivity, integration with microfluidic networks, and high-throughput analyses—high quality statistical inference due to poor resolution limits remains a key challenge. The devices and methods of the invention use multiple measurements on each molecule (e.g., DNA molecule) (Sen et al., 2012) to improve the statistical inference for identifying the desired (error-free) product (e.g., gene) in a background of products (e.g., PCA products) with high fidelity. Provided herein are new ways to isolate sub-populations of molecules (e.g., DNA molecules) akin to fluorescence-based flow cytometry. Application of a voltage bias across the membrane of the device drives an ionic current through the nanopore, and a measurable signal indicative of the structure and composition of a molecule is obtained as the molecule passes through the nanopore (Meller et al., *Physical Review Letters*, 2001, 86(15), 3435-3438; Kasianowicz et al., *Proc. Of the Natl. Acad. of Sci. USA*, 1996, 93(24), 13770-13773, each of which is incorporated herein by reference). The invention is useful for, inter alia, the extraction of a small population of desired molecules from a complex background where the ideal species may be in very low abundance. For example, the error rate involved in nucleic acid amplification (e.g., by polymerase chain reaction) is significantly less than that involved in chemical synthesis of oligonucleotides. Using the methods and devices of the invention to sort even a single or few error-free oligonucleotides with high purity may salvage potentially failed reactions, as the selected molecule can be subsequently amplified. Thus, the desired reaction products (molecules) may be extracted from reactions with very low yields of the correct molecule—reactions that would otherwise be rendered failures in conventional production modes.

Figure 14:
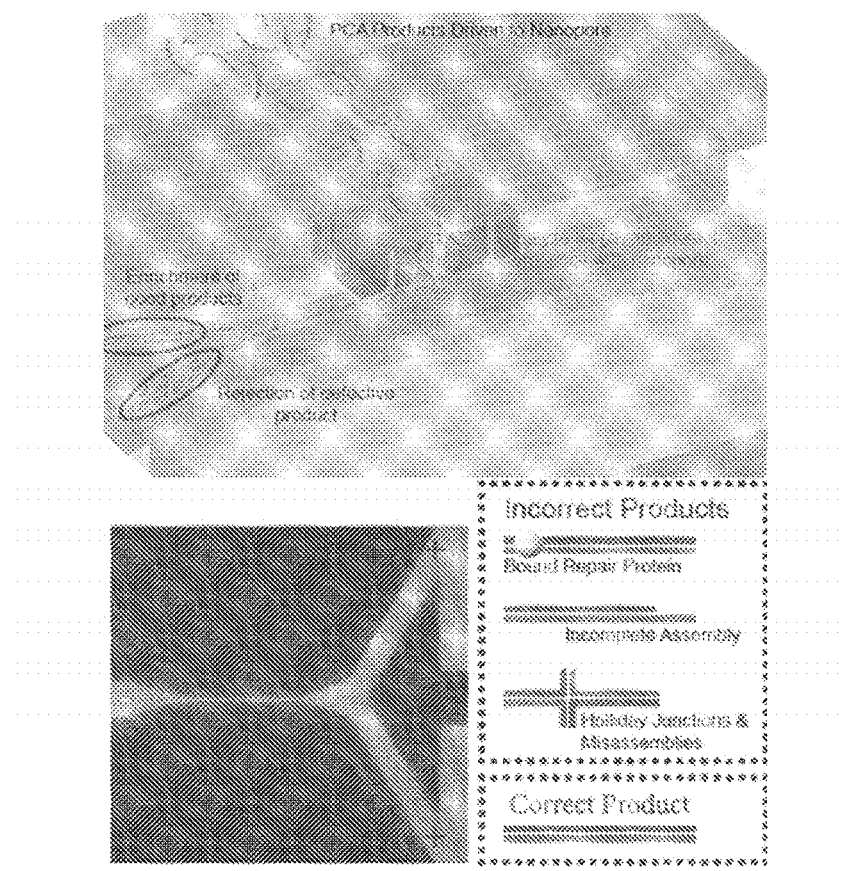
FIG. 14 shows an example of a device of the invention for analysis and sorting of gene synthesis products.

The methods and devices provided herein improve the signal-to-noise ratio by nearly eliminating substrate capacitive noise, and enable measurement of molecules at higher bandwidths. Combined with feedback control algorithms for multiple measurements on single molecules that have been developed (Sen et al. (2012)), the statistical inference on DNA molecule properties can be significantly enhanced. The integration of nanopores in microfluidic networks provides for molecules to be processed upstream (e.g., gene synthesis), and downstream (e.g., sorting the molecule based on nanopore sensor measurements). Thus, the present invention may be used to address key challenges of quality analysis, control, and purification posed by de novo DNA synthesis by using microfluidics integrated nanopore sensors to, inter alia, (i) identify errors in polymerase construction and amplification (PCA) products using DNA translocation signatures in nanopore devices, (ii) discriminate synthetic errors and point mutations in PCA products via sensing of repair protein-bound DNA, and (iii) select error-free genes by nanopore-enabled single molecule sorting (FIG. 14).

A "molecule" according to the invention encompasses a variety of molecules including, without limitation, biomolecules such as, for example, macromolecules, nucleic acids, proteins, amino acids, viruses and bacteria, and small molecules such as, for example, polysaccharides, lipids, glycolipids, sterols, glycerolipids, vitamins, hormones, neurotransmitters, metabolites and secondary metabolites.

As used herein, a "plurality" of molecules (e.g., nucleic acids) refers to a population (e.g., more than one) molecule. In some embodiments, a plurality of molecules according to the invention may be a heterogeneous or a homogenous population of molecules. For example, a heterogeneous population of nucleic acids may contain a mixture of nucleic acids of different lengths, different conformations (e.g., single-stranded, double-stranded), different chemical composition (e.g., DNA, RNA), or any combination of two or more of the foregoing. As another example, a heterogeneous population of molecules may comprises a mixed population of nucleic acids and proteins.

Molecules may be characterized and sorted based on their molecular characteristics. Such characteristics include, without limitation, length, conformation, and location of bound molecules (e.g., protein bound to DNA or other DNA binding elements). With regard to nucleic acids, in particular, the devices of the invention may be used to determine the difference between RNA and DNA (Wanunu, M. et al., *Nature Nanotechnology* 5 (11), 807-814 (2010), incorporated herein by reference), map bound peptide nucleic acid (PNA) molecules to DNA (Singer et al., 2012), and differentiate between single-stranded DNA (ssDNA) and double-stranded (dsDNA) (Singer, A. et al., *Nano Letters* 2010, 10(2), 738-742, incorporated herein by reference).

Unlike classic methods such as electrophoresis and sequence, which are unable to distinguish a small number of molecules from a larger population, the devices of the invention provide for analysis of a single molecule. As the molecule translocates (e.g., moves) through a nanopore, information regarding its characteristics can be recorded. Based on these characteristics, the molecule may then be sorted. An example of a two-step sorting process that may be used in accordance with the invention is as follows. In the first step, characteristics of a synthetic DNA molecule are determined by passage through a nanopore, as described elsewhere herein. In the second step, a decision is made, based on its molecular characteristics, whether the DNA is "good" (e.g., synthesized with the correct sequence) or "bad" (e.g., synthesized with a mutation). A "good" molecule is moved to one channel, and a "bad" is moved to another channel. For example, if a microchannel is configured with a "Y" junction, a "good" molecule may be moved to one side of the junction, and a "bad" molecule may be moved to the other side of the junction.

A signal indicative of structure, composition or a combination thereof may be recorded as a molecule translocates through a nanopore from one microchannel to another microchannel (see e.g., Wanunu, 2012). Multiple measurements of each molecule may improve the resolution of the nanopore sensor for monitoring specific types of errors introduced, for example, during synthetic gene construction, such as large-scale rearrangements, deletions, and point mutations.

DNA Repair Enzymes

Nanopore devices, in some embodiments, can be used to discriminate local sequence defects such as damaged bases, small insertions/deletions, and substitutions. One powerful method to enhance the ability of the nanopore to recognize these errors is to use the chemical specificity of DNA repair enzymes that recognize and bind defective sites. For example, MutS from *Thermus aquaticus* (Taq), can be used as a mismatch-binding protein to detect synthetic errors. Other examples of mismatch-binding proteins that may be used in accordance with the invention include, without limitation, human apurinic/apyrimidinic (AP) endonuclease (APE 1), endonuclease III (Endo III), endonuclease IV (Endo IV), endonuclease V (Endo V), endonuclease VIII (Endo VIII), formamidopyrimidine [fapy]-DNA glycosylase (Fpg), human 8-oxoguanine DNA N-glycosylase (hOGG1), human endonuclease VIII-like 1 (hNEIL1), T7 Endonuclease I (T7 Endo I), T4 pyrimidine dimer glycosylase (T4 PDG), uracil-DNA Glycosylase (UDG), Afu uracil-DNA Glycosylase (Afu UDG), human single-strand-selective monofunctional uracil-DNA glycosylase (hSMUG1), and human alkyladenine DNA glycosylase (hAAG). Each of the foregoing is commercially available, e.g., from New England BioLabs Inc., Ipswich, Mass.

EXAMPLES

Example 1

Device Fabrication

Photolithography (SU-8, Shipley) (e.g., soft lithography) was used to create a negative mold defining the microchannel system. Microchannel networks comprising larger access microchannels that taper into smaller microchannels (FIG. 1(c)(i)) were defined in polydimethylsiloxane (PDMS). The mold was chemically treated with 1H,1H,2H,2H-perflurododecyl trichlorosilane (Sigma Aldrich) for 6 hours prior to use. A 3:1 PDMS polymer:precursor ratio was poured over the SU-8 mold and cured for 8 hours at 80° C. The channels had widths of 8 µm and depths of 3 µm. The size of the smaller microchannels determined the membrane area exposed to the electrolyte solution, which may be tuned to, for example, less than 10 µm².

Next, commercially available 3-mm diameter transmission electron microscopy (TEM) grids (Ted Pella/TEM windows) with 50 nm thick Low Pressure Chemical Vapor Deposition (LPCVD) SiNx membranes (SiNx) with freestanding areas of 100 µm×100 µm on a silicon substrate were patterned with a focused ion beam (FIB) (FIG. 1(c)(ii)). Nanopores were drilled with a Ga⁺ FIB (Helios Nanolabs 600) in conjunction with NanoPattern Generating System (JC Nabity Lithography Systems) and were made with diameters of about 25 nm in a square array. The pitch between the nanopores was set to equal the microchannel width (3-8 µm) to increase the probability that a single pore in the device was registered between two microchannels (each microchannel in a different substrate). Cuts around the membrane (e.g., along the edge of the membrane) were made to promote membrane transfer to the receiving PDMS substrate. The patterned grid was then spatially located over the PDMS microchannel using a custom-built aligner and brought into conformal contact with the PDMS substrate. The flexibility of the polymeric substrate allowed for good contact with the grid even in the presence of particulates or debris. The patterned grid and the PDMS substrate were plasma bonded for 15 seconds at a pressure of 700 mTorr of air (atmospheric composition) at a power of 7.16 W. The TEM grid was peeled away, leaving behind a thin membrane covalently bonded above a microchannel (FIG. 1(c)(iii)). Another identical PDMS microchannel (rotated 90°) was plasma treated, positioned over the membrane in an identical fashion and brought into conformal contact such that a single nanopore electrically and fluidly connected the two microfluidic channels (FIG. 1(c)(iv)). Bonding between the two layers was achieved by exposing both surfaces to oxygen plasma (29.6 W, 700 mTorr, 1 min), utilizing PDMS to PDMS (substrate to substrate) bonding.

Thin conformal films of alumina ($Al_2O_3$) were deposited at 140° C. from alternating exposures of a precursor, trimethylaluminum ($Al(CH_3)_3$, TMA), and water at a growth rate of approximately 1.1 Å/cycle. $Al_2O_3$ depositions were performed as the last step after bonding the two PDMS substrates. $SiO_2$ ALD depositions were performed after membrane bonding and prior to bonding of the second PDMS piece by exposing the substrate to alternating exposure of TMA, water and three consecutive silane pulses at 140° C. Devices were baked for 3 days at 80° C. prior to use.

This modular fabrication/production process is amenable to large-scale integration and to different nanopore drilling schemes (e.g., TEM drilling, helium ion beam machining) and other substrate materials such as, for example, graphene (Kang, S. J., et al. *Adv. Mater.* 2011, 23, 3531-3535, incorporated herein by reference), hexagonal boron nitride (Novoselov, K. S., et al. *Proc. Natl Acad. Sci. USA* 2005, 102, 10451-10453, incorporated herein by reference) and ultrathin semiconductors (Merchant, C. A., et al. *Nano Lett.* 2010, 10, 2915-2921, incorporated herein by reference) as well as incorporation of metallic contacts within the lumen of the nanopore.

Electrical Characterization

The integrity of the devices were verified using electrical measurements. Current-voltage (I-V) curve measurements across a membrane without any nanopores confirmed that the suspended membrane was able to form a high resistance seal with the polymeric support. Using membranes with drilled nanopores, electrical characterization of the integrated devices demonstrated conductance values consistent with those expected from a single nanopore. FIG. 2(a) illustrates an example set of I-V measurements through a single 19 nm nanopore at different electrolyte concentrations. While the nanopore geometry is likely conical (see below), the linear I-V curves were consistent with expected values at low applied voltages.

Current traces were measured using an Axopatch 200B and digitized with a Digidata 1440 (Molecular Devices). Ag/AgCl electrodes (In Vivo Metric) were then inserted into the microchannel access ports. I-V curve measurements were taken by ramping the voltage from the maximum voltage down to its negative in 20 discrete steps. Traces were recorded at a cutoff frequency of 2 kHz and a sampling frequency of 20 kHz. RMS noise and Power Spectral Densities (PSD) were obtained by measuring 10 seconds of current data at 100 kHz measurement bandwidth at 0 applied voltage. PSD estimation was performed in Matlab. A 2M KCl (Sigma Aldrich), 0.2× Tris/Borate/EDTA (TBE) (Sigma Alrich) buffer at pH 8 was prepared using Nuclease/RNAase-free water. The ratio of KCl to TBE was kept constant across different salt concentrations used for measuring nanopore conductance.

For the translocation of a molecule to produce a detectable ionic current signature, the resistance of all current pathways in parallel to the nanopore must be much larger than the resistance of the nanopore itself. For this device, the resistance of any current pathways in parallel to the nanopore was much larger than the typical resistance of the nanopore. In order to measure the resistance in parallel with the nanopore, a negative control was performed in the absence of any pores in the membrane. The measured resistance provided information about the smallest resistance(s) that would be in parallel with the nanopore (had they been made). For a 110 nm thick membrane, and a salt concentration of 1M KCl, an access resistance of 753 MΩ was measured. This resistance is much larger than typical nanopore resistances, which are rarely larger than 50 MΩ.

It was hypothesized that this leakage current is caused by the imperfect ability of the top piece of PDMS to conform to the step jump in substrate height due to the membrane. Assuming a triangular profile for this alternate current pathway, the geometry of the profile is fully specified. There are two leakage paths (one on either side of the membrane), each of equal dimensions, e.g., channel length of 90 μm, height of 110 nm. An assumption of a channel cross-section of a 45°–45°–90° triangle lead to a predicted leakage resistance of 670 MΩ, which was close to the measured resistance.

Fluorescence Characterization

Figure 6:
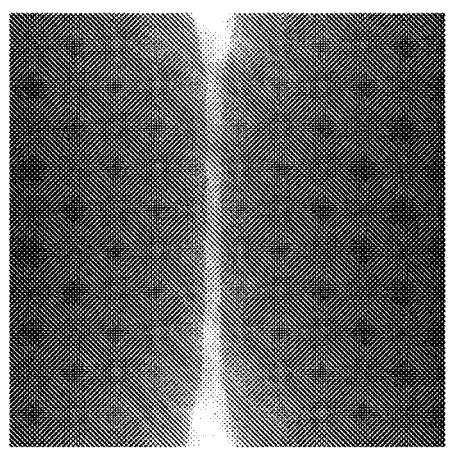
FIG. 6 shows the diffusion of dye in a different devise without a nanopore (membrane only) after five days.
Figure 7:
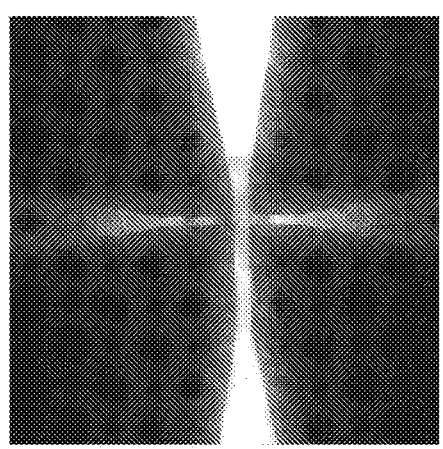
FIG. 7 shows the diffusion of dye in a device through a nanopore and into the microchannel after 4 hours.
Figure 8:
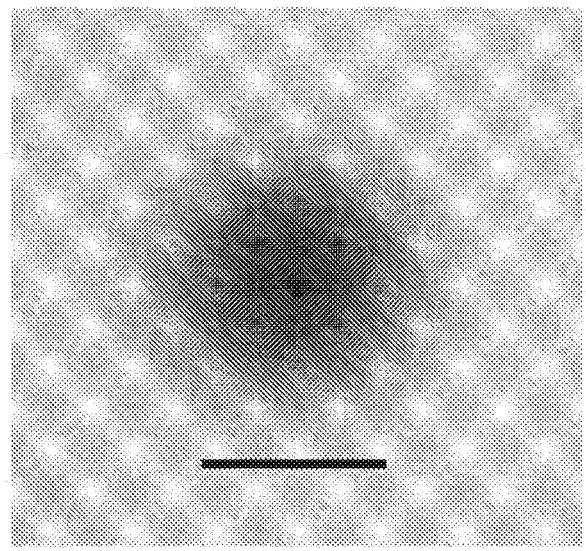
FIG. 8 shows a scanning electron microscopy SEM image of a Ga$^+$ Focused Ion Beam (FIB) nanopore. The scale bar is 50 nm.

The integrity of the devices were then verified using fluorescence measurements, which showed the absence of visible leakage pathways. A 100 mM, 0.01×TBE buffer at pH 8 was prepared with a concentration of 0.1 mg/mL of the fluorescent dye, Alexa Fluor 488 (MW 10,000)(Molecular Probes). The relatively large molecular weight of the molecule ensured that diffusion into the PDMS matrix was minimal. The membrane in the device did not contain any machined nanopores. A 1 V voltage bias was applied between the common ground and one of the outlets of the specified microchannel. The optical discharge of a mercury lamp, bandpass filtered at 465-495 nm, illuminated the device. An epifluorescence image was taken two days after the initial rinse. The device was imaged with a Nikon Eclipse TE-2000U optical microscope, with an emission bandpass filter of 515-555 nm. Images were taken less than one minute after application of the voltage across the nanopore (FIGS. 6-8).

Assuming a diameter of the molecule of roughly 1 nm, the diffusion coefficient can be approximated from the Stokes-Einstein equation to be $D \approx 2 \times [(10)]^{(-10)} m^2/s$. Further assuming one-dimensional diffusion for a time period of 1 day, the mean square displacement of dye molecules through any leakage channels is approximately $\sqrt{(\sqrt{x^2}\sqrt{})} = \sqrt{2Dt} = 6$ mm. Thus, a clear fluorescent signal from any alternate current pathways was expected.

Nanopore Geometry: Conductance Calculations

Figure 2:
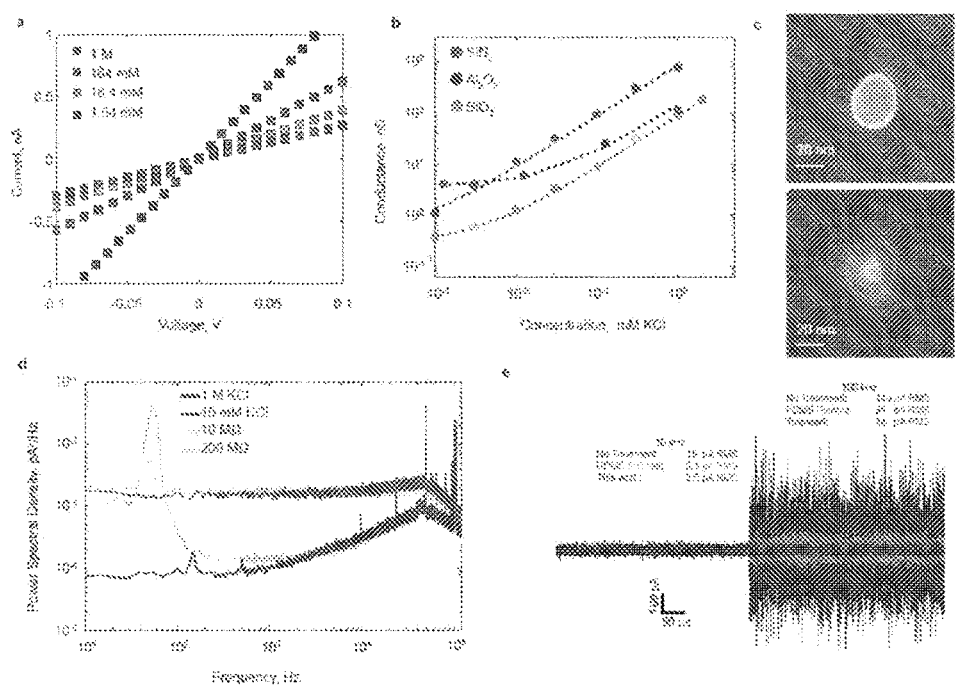
FIG. 2 shows a graph depicting data from the electrical characterization of an example configuration of a device of the invention. (a) I-V curves for 30 nm effective diameter $Al_2O_3$ nanopore at four electrolyte concentrations (1 M, 164 mM, 16.4 mM, 1.64 mM KCl). (b) Effect of concentration on conductance for different nanopore surface materials. The measured effective diameters were 72 nm, 20 nm, 19 nm, and surface charge was −2 mC/m2, −8 mC/m2, and +40 mC/m2 for SiNx, $SiO_2$ and $Al_2O_3$ nanopores, respectively. (c) TEM images of a nanopore before and after atomic layer deposition (ALD) of $Al_2O_3$. (d) Power-spectral density versus frequency at no applied voltage bias, sampled at 250 kHz and filtered at 100 kHz in 1 M KCl and 10 mM KCl in a 20 nm $SiO_2$ coated nanopore compared with 10 MΩ and 100 MΩ resistors. (e) Power-spectral density versus frequency at no applied voltage bias, sampled at 200 kHz and filtered at 100 kHz in 1 M KCl and 10 mM KCl of a 14 nm $Al_2O_3$ coated nanopore compared with 10 MΩ and 100 MΩ resistors sampled at 250 kHz and filtered at 100 kHz.

The flexibility of the fabrication approach was next illustrated by tuning the diameter and surface charge of the nanopore using atomic layer deposition (ALD) of alumina ($Al_2O_3$) and silicon dioxide ($SiO_2$). FIG. 2(*b*) demonstrates conductance as a function of electrolyte concentration for nanopores coated with $Al_2O_3$ and $SiO_2$ compared to an uncoated SiNx nanopore device. Fitting the data to a model for the conductance yields (see below) estimated values of the nanopore inner diameter and surface charge (72 nm, −2 mC/m2 for SiNx; 19 nm, 50 mC/m2 for Al2O3; 20 nm, −8 mC/m2 for SiO2). FIG. 2(*c*) shows TEM images of a Ga+ machined nanopore before and after ALD of alumina, which corroborates the higher resistances of the ALD nanopores observed with electrical measurements. Together, these results demonstrate the mechanical and electrical integrity of the membrane separating the two microchannels, thereby ensuring that the nanopore acts as the sole bridge.

Pore Geometry

Nanopores were made with a Ga+ Focused Ion Beam (FEI Helios). Previous TEM cross-section annular dark field micrographs (Patterson, N. et al., *Nanotechnology* 19, 235304 (2008), incorporated herein by reference) suggested a funnel-like geometry for nanopores fabricated with Ga+ ion beams in 200 nm thick SiNx membranes. For a conical frustum (or truncated cone), with top and base diameters, d1 and d2, height L, and a characteristic angle, α, the relationship between the diameters is given as:

$$d_1 = d_2 + 2L \tan \alpha$$

Concentration Dependence of Nanopore Conductance

The resistance of a conical frustum can be derived by integrating the differential resistance over dh from 0 to L:

$$dR = \frac{4\rho \, dy}{\pi d^2}$$

With $$d(y) = d_2 + \frac{(d_1 - d_2)}{L} y,$$

this expression yields:

$$R = \frac{4\rho L}{\pi d_1 d_2}$$

Or, in terms of the conductance:

$$G = \frac{\gamma \pi d_1 d_2}{4L}$$

Due to the similarity with the traditional formula for the resistance of a cylinder, an effective diameter can be defined as:

$$d_{eff} = \sqrt{d_1 d_2}$$

Following previously developed derivations (Schoch, R. B. & Renaud, P., *Applied Physics Letters* 86 (25), 253111-253111-3 (2005); Daiguji, H., Yang, P. & Majumdar, A., *Nano Letters* 4 (1), 137-142 (2004)), the concentration dependence of the conductance of a conical nanopore is derived. For a conical frustum, the total charge introduced into the nanopore can be calculated assuming electroneutrality.

$$N_e = \frac{\pi \sigma_s^*}{e} \frac{(d_1 + d_2)}{2} \sqrt{\frac{1}{4}(d_1 - d_2)^2 + L^2}$$

And the nanopore volume averaged number density of excess ions in the nanopore is:

$$c_{excess} = \frac{4\sigma_s^*}{L}\frac{10^{-3}}{N_Ae}\frac{3(d_1+d_2)}{2(d_1^2+d_1d_2+d_2^2)}\sqrt{\frac{1}{4}(d_1-d_2)^2+L^2}$$

For convenience, a dimensionless geometric factor is defined as:

$$\kappa_\sigma = \frac{(d_1+d_2)\sqrt{\frac{1}{4}(d_1-d_2)^2+L^2}}{(d_1^2+d_1d_2+d_2^2)}$$

Substituting:

$$c = c_{bulk} + c_{excess}$$

With the conductivity being:

$$\gamma = 10^3 N_A e \Sigma_i \mu_i c_i$$

Thus, the conductance of a conical frustum becomes:

$$G = \frac{\pi d_1 d_2}{4L}\left[10^3(\mu_+ + \mu_-)c_{bulk}N_A e + 6\frac{\mu_c \sigma_s^* \kappa_\sigma}{L}\right]$$

Noise Estimates

Sensing nucleic acids and other biomolecules with nanopore systems is generally limited by two coupled parameters: sampling bandwidth and system noise. Increasing the sampling bandwidth to more accurately detect current changes through the nanopore is accompanied with an increase in system noise. Previously developed noise models for nanopore systems, demonstrated that capacitive noise was the dominant noise source at high sampling bandwidths (10-100 kHz) and that a nanopore system with negligible capacitance would produce noise characteristics equivalent to an ideal resistor at high frequencies (see below). The total system noise of the devices of the invention coated with $SiO_2$ were compared to resistors with low capacitance (<1 pF) by studying the power spectral density (PSD). The medium gray curves (top, 1 M KCl) in FIG. 2(d) demonstrate that at low nanopore resistances, the PSD consists of a flat white noise spectrum whose magnitude is determined by the thermal fluctuations commensurate with the resistance of the pore. The similarity of the dark gray curves (bottom, 10 mM KCl) in FIG. 2(d) demonstrates that at higher nanopore resistances, the dominant noise contribution comes from the measurement amplifier and not from the device itself. The same trends are observed for an $Al_2O_3$ coated nanopore (see below), thereby demonstrating that the surface properties (and low frequency noise) can be tuned without altering the capacitance (and high frequency noise). The elimination of capacitive noise decreased total system noise from roughly 30 pA RMS to 15 pA RMS at 100 kHz bandwidth (FIG. 2(e)). The obtained noise levels are in contrast to nanopores on a silicon substrate, where parasitic capacitance causes the high-frequency noise to significantly exceed that of a resistor (Uram, J. D., et al. *ACS Nano* 2008, 2, 857-872, incorporated herein by reference). The enhanced noise performance of the device of the invention can be explained by an increase in the impedance and a concomitant decrease of the effective parasitic capacitance of the current pathways in parallel with the nanopore due to the integrated design architecture. The parasitic capacitance in typical nanopore devices comes from two leakage pathways: the electrolyte-Si-electrolyte pathway, and the electrolyte—SiNx membrane—electrolyte pathway. In the devices of the invention, the underlying silicon support wafer, which has a relatively high dissipation factor (Smeets, R. M. M. et al. *Proc. Natl Acad. Sci. USA* 2008, 105, 417-421, incorporated herein by reference) has been replaced by a low dissipation factor material (PDMS has a low dissipation factor similar to that of quartz). Secondly, the area of the membrane exposed to the electrolyte solution is restricted by the width of the microfluidic channels (9-64 μm²), which decreases the total capacitance of the SiNx membrane. The noise in the devices is thus limited primarily by the measurement noise and can decrease further with the use of low-noise integrated amplifiers (Rosenstein, J., et al. *Nature Meth.* 2012, incorporated herein by reference). In contrast to previous schemes to reduce capacitance and system noise using elastomer gaskets (Tabard-Cossa, V., et al. *Nanotechnology* 2007, 18, 305505, incorporated herein by reference) or multi-layer membranes (Dimitrov, V., et al. (2010)), which limit the system to a single nanopore, the present configuration utilizes a single step to directly embed a low-noise nanopore (or multiple low-noise nanopores at the same time) into a microfluidic system, which can also provide upstream and downstream processing of molecules.

Several sources of noise have been explored in nanopore devices. These sources are low frequency (flicker, F) noise, thermal noise at equilibrium (E) and noise from the measurement instrument (M). Assuming these sources of noise are independent of each other, they can be added in quadrature, yielding a formula for the total noise in the setup:

$$\delta I_{Total}^2(f)df = \delta I_E^2(f)df + \delta I_F^2(f)df + \delta I_M^2(f)df$$

Modeling the nanopore as a single resistor in parallel with a lumped circuit leaky capacitor (constant phase element), the following expression was obtained for the equilibrium noise contributions:

$$\delta I_E^2(f)df = 4kT\left(\frac{1}{R} + \pi CDf\right)df$$

This can be divided into a resistive component and a capacitive component, where the resistive noise can be described as:

$$\delta I_R^2(f)df = 4kT\left(\frac{1}{R}\right)df$$

The capacitive noise can be described as:

$$\delta I_C^2(f)df = 4kT(\pi CDF)df$$

The low frequency or flicker noise follows Hooge's phenomenological relationship, with a Hooge's constant of $1.1 \times 10^{-4}$ for $SiN_x$ nanopores (Kowalczyk, S. W., et al. *Nano Lett.* 2010, 10, 324-328; Li, J., et al. *Nature* 2001, 412, 166-169, each of which is incorporated herein by reference).

$$\delta I_F^2(f)df = \frac{\alpha I^2}{N_C f}df$$

Lastly, the noise from the measurement instrument can be described as (Storm, A. J., et al. *Nature Mater.* 2003, 2, 537-540, incorporated herein by reference):

$$\delta I_M^2(f)df = \left(2qI_{FET} + 4kT_h\frac{a}{R_f} + e_n^2\left[\frac{1}{R_f^2} + (2\pi Cf)^2\right]\right)df$$

Figure 9:
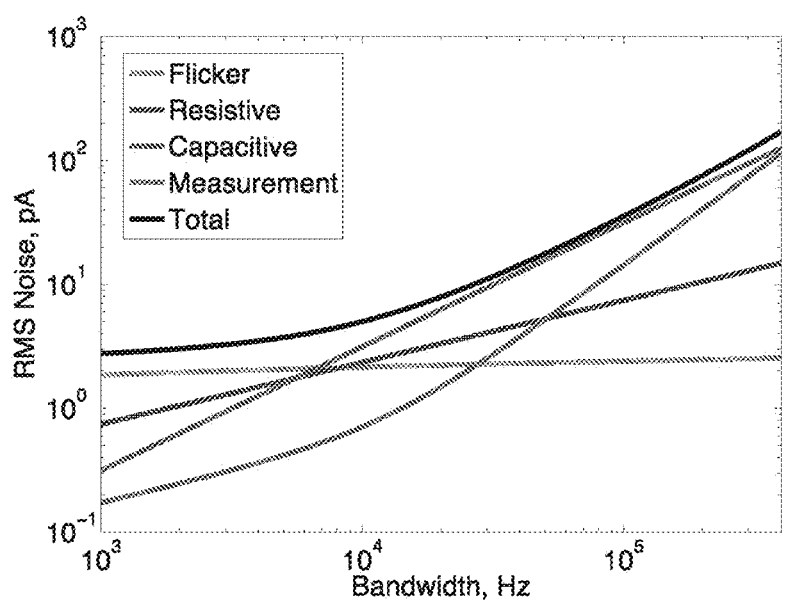
FIG. 9 shows a graph depicting noise estimates for typical solid state nanopores as a function of bandwidth.
Figure 10:
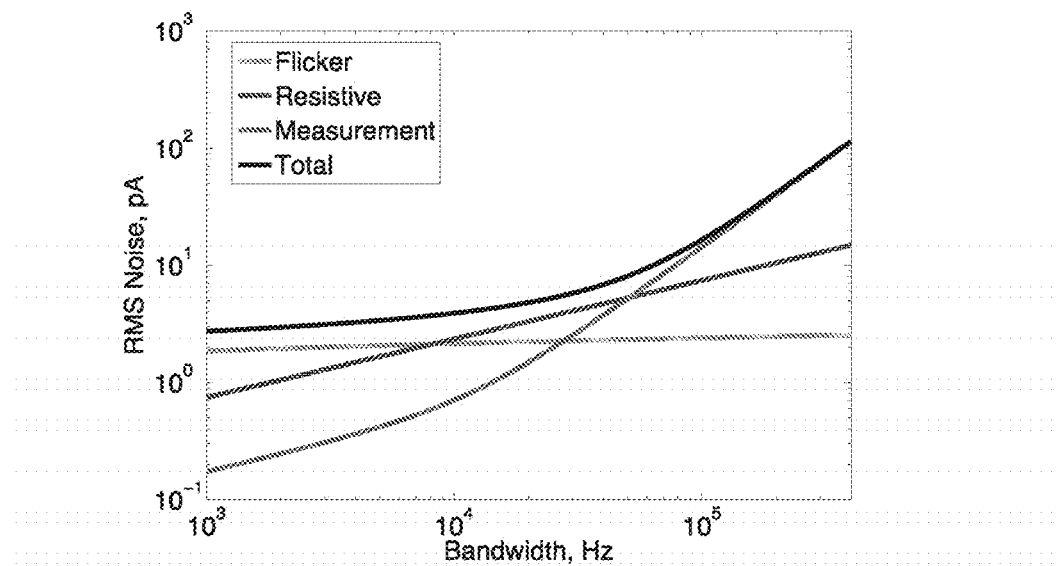
FIG. 10 shows a graph depicting noise estimates for solid state nanopores in the absence of parasitic capacitances.
Figure 11:
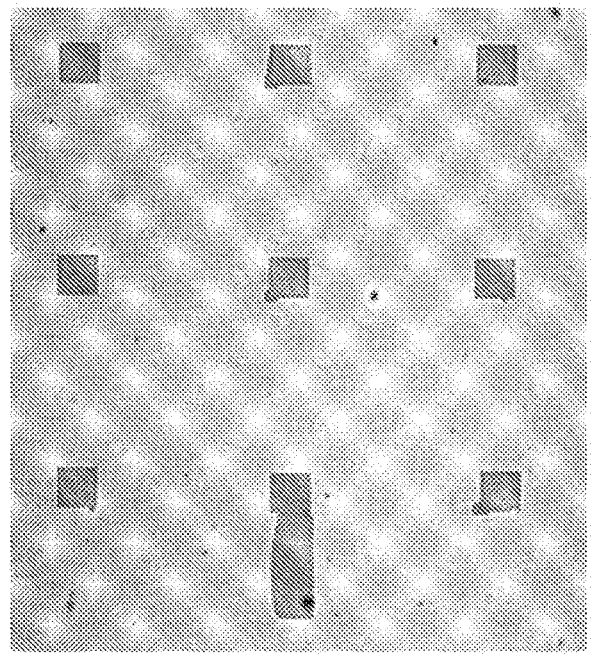
FIG. 11 shows an image of nine square membranes transferred to a single polydimethylsiloxane (PDMS) substrate, where each square membrane is 90 μm×90 μm. Scale bar is 100 μm.

Previous noise measurements in nanopore devices (Tabard-Cossa, V., et al. *Nanotechnology* 18, 305505 (2007); Smeets, R. M. M., et al. (2008), each of which is incorporated herein by reference), suggested that, in the absence of any membrane treatment (deposition of insulating spacers between solution and the membrane), parasitic capacitance from the silicon wafer and the membrane dominated noise above bandwidths of 10 kHz. Noise has been reduced (Fologea, D., et al. *Nano Lett.* 2005, 5, 1734-1737, incorporated herein by reference) at higher bandwidth (100 kHz) by adding an SiO$_2$ spacer between the nitride and silicon wafer. For the purposes of modeling noise in these devices, typical nanopore devices are assumed to have a capacitance of 7 pF, and a dissipation factor of 0.27 (Smeets, R. M. M., et al. 2008). This assumption yields a capacitive contribution to RMS noise of approximately 30 pA, which is achievable in nanopore sensors usually after performing several microfabrication steps (Wanunu, M. et al., 2010; Dimitrov, V. et al., (2010), each of which is incorporated herein by reference). In FIG. 9, the contribution of each noise source to the total RMS noise has been integrated over frequency (taking into account the additional constants arising from the Bessel filter (Uram, J. D., Ke, K. & Mayer, M., *ACS nano* 2 (5), 857-872 (2008)), and is plotted as a function of bandwidth.

Thus, in the absence of membrane capacitance, the noise properties of the microfluidic-integrated nanopore system could be approximated by the noise properties of an ideal resistor. An ideal resistor is defined by the fact that the only relevant sources of noise are the resistance and measurement noise. Because noise sources add in quadrature, low frequency and capacitive noise do not contribute significantly to the total noise:

$$\frac{\int \delta I_F^2(f)df}{\int \delta I_{Total}^2(f)df} \ll 1$$

$$\frac{\int \delta I_C^2(f)df}{\int \delta I_{Total}^2(f)df} \ll 1$$

In order to verify this claim, high quality resistors with <1 pF capacitance were compared to the devices of the invention. The PSD of the resistors was measured and directly compared to the PSD of nanopore devices fabricated as described herein.

Below resistances of roughly 13 MΩ, resistive noise is the dominant source of noise at 100 kHz cutoff frequencies. At higher resistances, the measurement instrument (the amplifier) is the dominant source of noise.

Multiple Membrane Transfer

Figure 12:
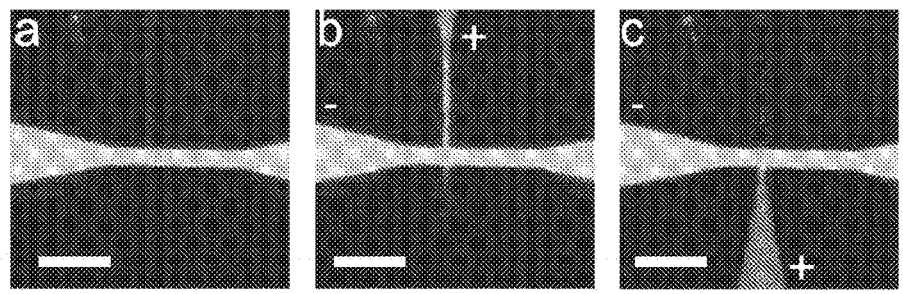
FIG. 12 shows fluorescent images of directional dye transport through nanopore and microchannels where the scale bar is 40 μm.

A unique feature of the fabrication process of the invention is the ability to "transfer print" multiple membranes onto a single layer of channels or a single membrane onto multiple channels. The TEM grids used in the experiments contain nine windows of dimensions, each about 100 μm×100 μm. FIG. 12 shows all nine membranes transferred to a single PDMS substrate.

The transfer-printed membranes may also be placed on different planes with three-dimensional inlet and outlets. In the configuration presented in this example, which places the thin membrane on the neutral mechanical plane (NMP) between two bonded PDMS slabs, the device can tolerate mechanical deformations without membrane cracking. These features of three-dimensional complexity (embedded access channels) and robustness (tolerance to varied mechanical inputs) are also observed in self-assembled systems such as tissues and plants. A vital building block towards construction of these higher complexity systems is the ability to regulate molecular transport between layers and spatially address specific locations.

To demonstrate these capabilities, two experiments were performed, whereby in the first experiment (see Example 2), a nanopore was used to regulate fluid transport between adjoining microfluidic channels and switch molecules passing through the nanopore into either of two outlets (Supplementary Section S5). The second experiment (Example 3) demonstrates the electrical addressability of individual nanopores in an array of nanopores and the ability to control transport between different microchannels Example 2

In this example, a single nanopore and membrane were used to actively regulate molecular transport between adjoining microfluidic channels. FIGS. 12(a)-12(c) show a series of optical microscopy images where a fluorescent dye (Alexa 488) was introduced into the top microchannel. When no voltage bias was applied, dye remains in the top channel and does not actively transport through the nanopore (FIG. 12(a)). As a voltage bias was applied across the membrane, the dye electrophoretically moved into and through the nanopore to the lower microchannel (FIG. 12(b)). Moving the opposite bias from one end of the lower microchannel to the other end changed the direction of flow (FIG. 12(c)).

It is clear from this example that application of a voltage bias induces active transport of the dye through the nanopore. Furthermore, the direction of the molecular species through the microchannel is controlled by the placement of the electrode. Alternatively, pressure driven flow could be used to directionally transport fluid (and dye with it) away from the nanopore after translocation.

Example 3

Figure 3:
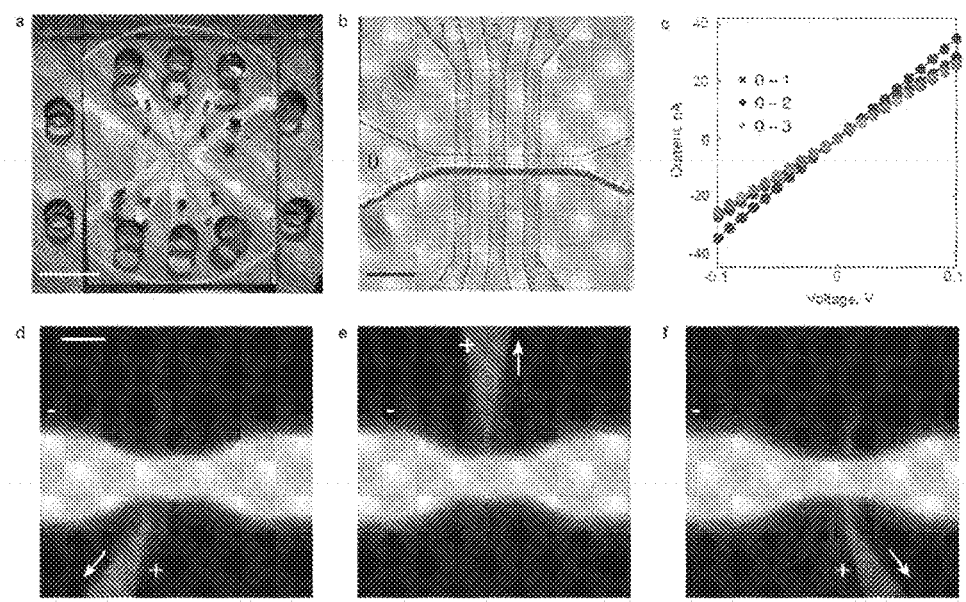
FIG. 3 depicts an example configuration of a device of the invention. (a) Photograph of a device of the invention, scale bar 2 mm. (b) Optical micrograph of membrane with nanopore array embedded between polymeric substrates having microchannels. Numbering indicates the placement of electrodes for electrical measurements through nanopores. Scale bar 30 µm. (c) I-V curve measurements between common ground and source microchannels at 2 M KCl. (d) False color image of fluid transport of a fluorescent dye in the device after application of voltage between the common ground {0}and the bottom outlet of the source microchannel {1}. (e) After application of voltage between the common ground {0}and the top outlet of the source microchannel {2}. (f) After application of voltage between the common ground {0}and the bottom outlet of the source microchannel {3}. Scale bars in (d-f) are 50 µm.

Next, a device (FIG. 3(a)) containing three nanopores was produced. Each nanopore was connected to a common microchannel that acts as a ground (microchannel 0, FIG. 3(b) and a separate microchannel that acts as a source (microchannels 1-3, FIG. 3(b)). I-V curve measurements across each of the three microchannel intersections revealed resistances characteristic of single nanopores (FIG. 3(c)). As the applied voltage bias was moved from one microchannel to the next (FIGS. 3(d)-3(f)), transport of a fluorescent dye (Alexa 488) was directed through the corresponding nanopore and into the adjoining microchannel. Using a nanopore to act as a multi-level interconnect between microchannels on different planes enabled each channel to function as an isolated environment, whereby the nanopore electrically regulated transport between each compartment (Kuo, T. Z., et al. *Anal. Chem.* 2003, 75, 1861-1867, incorporated herein by reference). This feature opens up new possibilities in multiplexed biosensing where sample preparation, labeling and readout can occur on different channels or planes.

Example 4

The functionality of the devices for sensing single double-stranded DNA (dsDNA) molecules was demonstrated next.

Figure 4:
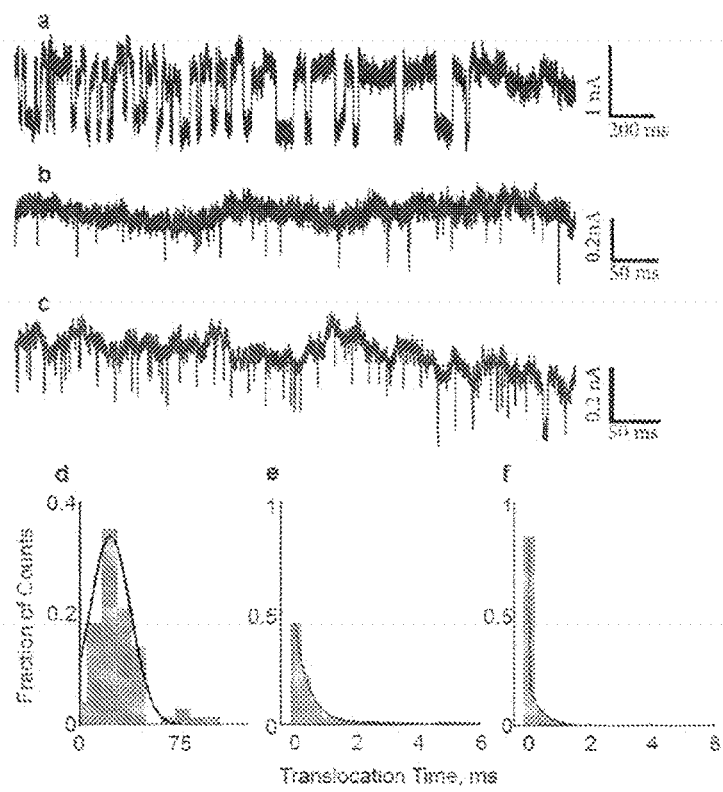
FIG. 4 shows a graph depicting results from recordings of a single DNA molecule passing through a nanopore of the device. Concatenated current traces for (a) λ-DNA (48502 bp), in a 1 M KCl, translocating through an 19 nm $Al_2O_3$ coated nanopore at 1 V. Scale bars are 1 nA and 500 ms. (b) 1 kbp DNA, in a 1 M KCl buffered solution, translocating through a 14 nm $Al_2O_3$ coated nanopore at 300 mV. Scale bars are 200 pA and 50 ms. (c) 1 kbp DNA, in a 2 M KCl buffered solution, translocating through a 20 nm $SiO_2$ coated nanopore. Scale bars are 200 pA and 50 ms. (d) Translocation time histogram for λ-DNA. The black line represents a single Gaussian fit to the data. (e) Translocation time histogram for 1 kbp DNA through a 14 nm $Al_2O_3$ coated nanopore with a double exponential fit (red line). (f) Translocation time histogram for 1 kbp DNA through a 20 nm $SiO_2$ coated nanopore with a double exponential fit (blue line).
Figure 5:
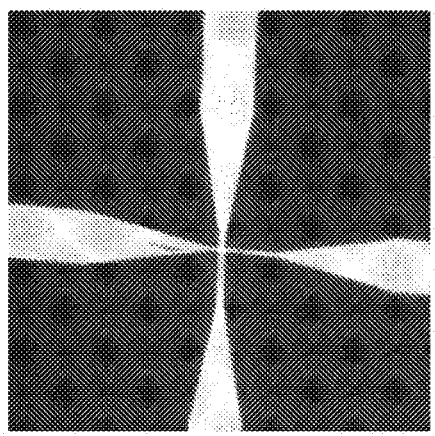
FIG. 5 shows the fluorescence leak test for a membrane only device: no alternative pathways are visible due to diffusion of the dye.

Nanopores with two different surface coatings, $Al_2O_3$ and $SiO_2$, were tested with DNA molecules of different lengths ranging from 1000 base pairs (bp) to 48,502 bp. A solution (100 ng/mL) of homogenous DNA molecules (1 kilobase (kbp), Fermentas) in electrolyte were loaded into a microchannel. Data from the $SiO_2$ nanopore were taken with an electrolyte concentration of 2 M KCl, 0.2× TBE. Data from the $Al_2O_3$ nanopores were taken with an electrolyte concentration of 1 M KCl, 0.1× TBE. Ag/AgCl electrodes were then inserted into the microchannel access ports, and a voltage applied across the nanopore. The ionic current was filtered with an 8-pole Bessel filter at 10 kHz and sampled at 25 kHz. 48,502 base pair (bp) lambda phage DNA (λ-DNA) solution at a DNA concentration of 1 µg/mL in 1 M KCl was also used, and the data was filtered at 5 kHz, and sampled at 20 kHz. The amplitude and duration of DNA translocations were measured off-line and statistics were compiled to generate histograms in FIG. 4.

Translocation of single 48.5 kbp dsDNA molecules through a 19 nm diameter $Al_2O_3$-coated nanopore exhibited current blockade characteristics consistent with those previously reported (FIGS. 4(a) and 4(d)). The DNA translocation times (td) showed a broad distribution with a median value of 24.9 ms (~1.9 bp/µs). Multiple current blockade levels were also observed, which have been shown to arise from folded conformations of long DNA molecules translocating through the pores. A concatenated series of translocations of 1000 bp dsDNA fragments through a 14 nm diameter $Al_2O_3$ nanopore is shown in FIG. 4(b). In contrast to the 48,502 bp molecules, translocation times of the 1000 bp molecules exhibited a biexponential distribution (FIG. 4(e)). The shorter timescale of the biexponential distribution is associated with rapid DNA transport through the center of the nanopore (τshort=480 µs) and the longer timescale is correlated with translocations that saw more interaction with the nanopore (τlong=4.80 ms) (Storm, A. J., et al. *Phys. Rev. E* 2005, 71, 051903, incorporated herein by reference). The median translocation time of 240 µs (~4 bp/µs) for the 1000 bp molecule corresponds to a translocation speed two times faster than that of the larger DNA molecule, which is consistent with the drag forces imposed by the DNA chain outside the pore in case of larger molecules. 1000 bp DNA translocations were also detected in 20 nm diameter $SiO_2$-coated nanopores (FIG. 4(c)), showing a biexponential distribution of translocation times (FIG. 4(f)). The translocations occurred on a shorter timescale (τshort=110 µs, τlong=420 µs) with a 6-fold faster translocation speed (40 µs median translocation time, ~25 bp/µs) compared to that seen in $Al_2O_3$ nanopores. The DNA translocation velocities observed in these experiments were consistent with previous reports on $SiO_2$-coated38,39 and $Al_2O_3$-coated (Chen, P., et al. (2004); Venkatesan, B. M., et al. (2010)) nanopores and the difference between the two materials is attributed to the positive and inhomogeneous surface charge on $Al_2O_3$ that can slow down translocating DNA molecules.

Example 5

Figure 15:
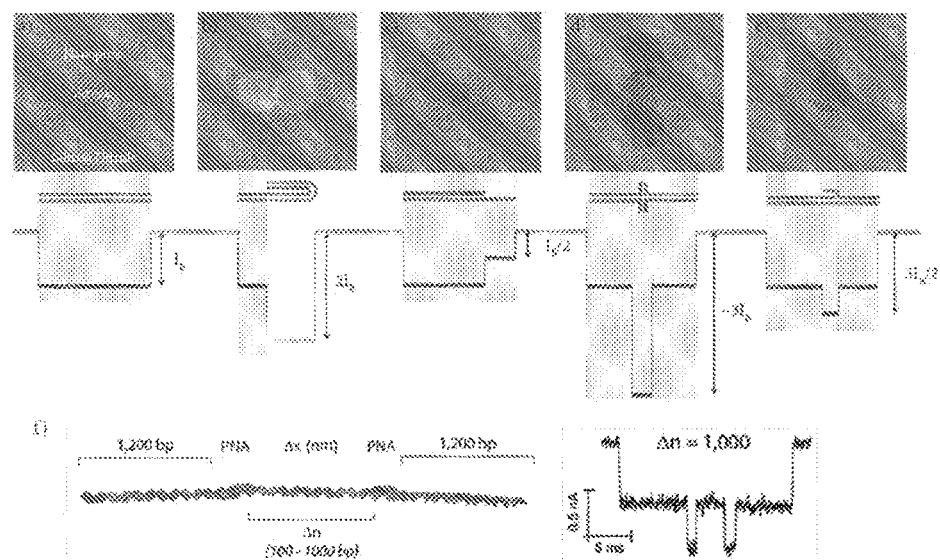
FIG. 15 shows expected translocation profiles for typical PCA products: (a) double stranded DNA (dsDNA), (b) folded ds DNA, (c) dsDNA with a single-stranded overhang, (d) Holliday junction, (e) dsDNA with single stranded overlap, and (f) signal produced by 3.2 kbp DNA with two PNA probes bound to 15 bp each (from Singer et al., Nano Letters, 2012, 12(3), 1722-1728, incorporated herein by reference).

The aim of this experiment is to identify correctly assembled polymerase construction and amplification (PCA) products, on a single molecule level, with high confidence using a nanopore device of the invention. By correct assembly, structural errors as opposed to sequence errors are implied. The translocation signatures of correctly assembled molecules (FIGS. 15(a) and 15(b)) are fundamentally different from those of PCA products that are misassembled and, therefore, structurally different (major misassembled products are depicted in FIGS. 15 (c),(d),(e)) due to variations in the cross sectional area of the PCA product translocating through a nanopore. Specifically, each kind of misassembled molecule has a translocation signature that has a distinct sequence of steps (FIGS. 15 (c),(d),(e)), based on which algorithms to reject the misassembled molecule are developed. Any translocation signature that is statistically different from that expected from the correctly assembled molecule can be rejected and labeled a structural defect, regardless of whether the precise structure of the defect can be inferred. Statistically, for a given threshold criterion to identify a correctly assembled molecule, the probability of a false positive is sufficiently low (~1%). The synthesis of the 993 bp enhanced green fluorescent protein (EGFP) gene is used as a model, where PCA has a typical correct gene fraction of 19%.

To obtain high quality signals from translocating molecules, nanopores are fabricated using a Helium Ion Microscope, which has the ability to machine nanopores down to 4 nm (Yang, J. J.; et al., *Nanotechnology* 2011, 22(28), 285-310, incorporated herein by reference). If necessary, further nanometer scale fine-tuning of nanopore diameter are performed using atomic layer deposition (ALD) (Chen, P. et al., *Nano Letters*, 2004, 4, (7), 1333-1337, incorporated herein by reference). Nanopore diameters are verified with a transmission electron microscope. The translocation signatures of dsDNA molecules are first characterized in the range of 300-2500 bases to determine the nanopore diameter and material ($SiO_2$, SiNx, or $Al_2O_3$) that provides the best signal. Given the small nanopore diameter, the conformation of DNA molecules are limited to straight and double folded (FIGS. 15(a),(b)). Next, high purity ~1 kilobase pair (kbp) DNA molecules (positive control) are purchased, and the following negative controls are synthesized: (a) synthetic DNA molecules of the same length with overhangs of different size (50, 100, 200 bp), (b) dsDNA molecules with lengths 95%, 90%, and 70% of the control, and (c) synthetic Holliday junctions resulting from hybridization of four unique DNA strands (Rass, U. et al., *DNA Repair, Pt a* 2006, 408, 485, incorporated herein by reference). The translocation signals of these molecules are analyzed and algorithms developed to identify a correctly assembled molecule. Next, the PCA product (993 bp EGFP gene (positive control)) is mixed with the negative controls in varying (known) ratios to test whether the algorithm can correctly quantify the fraction and concentration of the correct product by measuring the frequency of detection of the correct and incorrect molecules, using capture rate data in the negative control to correct for the DNA length dependence of the capture rate (Wanunu, M. et al. 2010). Next, the concentration and fraction of the correctly assembled product is compared with the fraction quantified by gel electrophoresis. A significant discrepancy between the two suggests either that some misassembled products are unable to translocate due to the small pore size, or that structural defects cannot be properly resolved in the sensor. The experiments are repeated with slightly different nanopore size (±1 nm). Support for the feasibility to detect misassembled molecules is provided by the ability of nanopores to detect single-stranded PNA molecules bound to DNA (FIGS. 15(f)) (Singer, A. et al., 2012; Singer, A. et al., 2010).

To improve the fidelity of measurement and improve the ability to differentiate structural anomalies in PCA products, the DNA molecule is captured after translocation, and is measured multiple times (e.g., >25 times). To aid in performing multiple measurements on small molecules, the time between the translocation detection and voltage reversal is decreased to roughly 250 microsecond (μs) (enabled by Field-Programmable Gate Array (FPGA) control). To enhance DNA recapture probabilities for multiple measurements, smaller microchannels are used to better confine electric fields at the entrance of the pore.

Multiple measurements discriminate between dynamic conformations of a DNA molecule (which are randomly sampled upon each measurement made), and structural differences (which are unlikely to change between measurements). This method should significantly increase the confidence level in the inference of a structural defect. Furthermore, it is possible that there will be a small fraction of incomplete assembly products that are double stranded (similar to FIG. 15(a) in translocation), but are shorter than the target gene. In this case, the length of the incomplete dsDNA is typically at least 10% shorter than the gene length, determined by the length of oligonucleotides that are used for its assembly. Thus, the ability to estimate DNA length, even to within 10%, is extremely useful. It is anticipated that a ~20% length resolution for 25 measurements and ~10% resolution for 100 measurements on the same molecule are achieved. Length resolution with nanopore sensors are determined by measuring known dsDNA molecules from 300 to 2500 bp. The results are compared with electrophoresis.

Example 6

The aim of this experiment is to use nanopore devices to discriminate local sequence defects such as damaged bases, small insertions/deletions, and substitutions. In contrast to length or structural differences, small defects such as point defects may not result in detectable changes in the DNA translocation signal of the gene. One powerful method to enhance the ability of the nanopore to recognize these errors is to use the chemical specificity of DNA repair enzymes that recognize and bind defective sites.

MutS from *Thermus aquaticus* (Taq) is used as a model mismatch-binding protein to detect synthetic errors. Taq MutS is an 89 kilodalton (kDa) protein, with an elongated shape (longest dimension about 10-12 nm). MutS is part of the DNA repair pathway in a variety of organisms, and binds to all simple single base mismatches and insertions or deletions up to 4 base pairs long in double stranded DNA. MutS affinity is known to vary with type of mismatch, and in some species, such as *E. coli*, certain mismatches (e.g., CC) are not bound with greater affinity than homoduplex DNA. Taq MutS binding can be employed to discriminate all types of single base mismatches and insertions/deletions of various lengths (in one case as much as a 50 bp deletion) (Carr, P. A. et al., *Nucleic Acids Research*, 2004, 32(20), e162, incorporated herein by reference). This procedure dramatically improved the quality of the synthetic DNA products yielding a 15-fold reduction in error rate (i.e., MutS identified ~90% of the errors).

Figure 16:
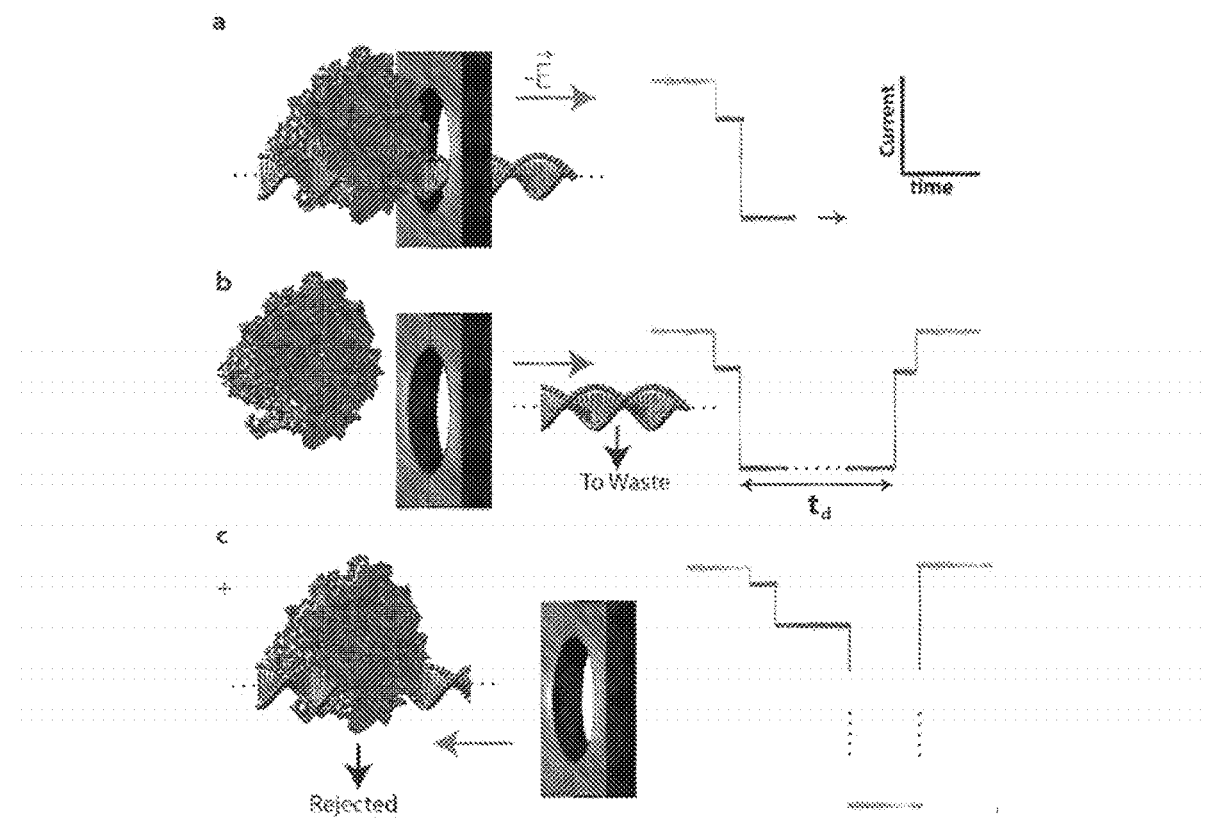
FIG. 16 shows MutS situations and corresponding expected current traces (a) DNA-MutS complex lodged in a nanopore, (b) translocation of DNA after dissociation of MutS, and (c) rejection of MutS by voltage reversal.

First, ~1 kbp long dsDNA is synthesized with engineered defectives sites (single base mismatch and 1 base deletion) that are known to bind MutS with relatively lower and higher affinity, respectively (Whitehouse, A. et al., *Biochemical and Biophysical Research Communications*, 1997, 233(3), 834-837, incorporated herein by reference). The molecules are incubated with MutS, and the resulting mixture comprising primarily of MutS and MutS-bound DNA is analyzed using the nanopore devices of the invention. Next, a mixture of the positive control (correct DNA, see Example 5) and the dsDNA with the defective site are mixed in a known ratio, and the ability of the nanopore to quantify the ratio of the two molecules is assessed. Bound structures such as proteins (Kowalczyk, S. W. et al., *Nano Letters*, 2010, 10, (1), 324-328, incorporated herein by reference) or small molecules and chemical modifications such as methylation (Wanunu, M. et al., *Journal of the American Chemical Society*, 2011, 133(3), 486-492, incorporated herein by reference) have been shown to yield measurable modulations of the current blockade levels when the nanopore diameter is sufficiently large to allow the complex to pass through. By using nanopore diameters of 13-15 nm, the MutS-DNA complex can translocate, and the percentage of MutS bound DNA should be detectable by the nanopore (Kowalczyk, S. W. et al., *Nano Letters*, 2010, 10(1), 324-328, incorporated herein by reference), allowing quantitative comparison of the results with the original ratio in which the molecules were mixed. While large pore sizes may suffice for quantification of MutS bound DNA, smaller nanopore diameters (~5-6 nm) are used to detect both sequence errors and structural defects within the same pore (as described in Example 5). With these nanopores, the MutS bound DNA is initially stuck in the nanopore (FIG. 16(a)) causing long translocation duration; the MutS may eventually dissociate from the DNA (FIG. 16(b)) if the voltage bias is maintained; or the voltage can be reversed (FIG. 16(c)), thereby driving the MutS-bound DNA away from the nanopore (e.g., a rejection). A secondary voltage across the microchannel can then be applied to further distance the MutS bound DNA from the vicinity of the nanopore. This process is easily automated similar to feedback control (Sen, Y. et al. 2012).

Next, the products of the PCA reaction for the EGFP gene are incubated with MutS to enable it to bind to defective regions of the double stranded DNA. The mixture is introduced into the nanopore device and the concentration and fraction of MutS-bound DNA is quantified using the developed algorithm. The quality of this PCA product is assessed with an Electrophoresis Mobility Shift Assay (EMSA) (Carr, P. A. et al., 2004) and directly compared with the nanopore analysis. As minimal sample prep is required to perform the nanopore assay, such a system can be directly coupled with existing microfluidic synthetic platforms for on-chip, automated analysis of the quality and purity of PCA products in near real-time and with concentrations far below those required for current electrophoresis techniques. The nanopore analysis is performed at the single molecule level, which opens the possibility of selecting out single defect-free DNA molecules from a pool of primarily defective products. Desired discrimination of DNA may also be used. For example, a number of Holliday junction resolvases have been shown to act as mismatch-cleavage nucleases, converting defective DNA heteroduplexes into shorter DNA species. These include commercially available T7 endonuclease I (Huang, M. et al., *Electrophoresis*, 2012, 33(5), 788-796, incorporated herein by reference), *E. coli* endonuclease V (Pincas, H. et al., *Nucleic Acids Research*, 2004, 32(19), e148, incorporated herein by reference), and celery Cel-I (Saaem, I. et al., *Nucleic Acids Research*, 2012, 40(3), 1-8; Tsuji, T. et al., *Electrophoresis*, 2008, 29 (7), 1473-1483, each of which is incorporated herein by reference). Using such enzymes with nanopore analysis provides for discrimination of the desired species represented by the surviving (uncut) full-length fraction of DNA in the sample.

Example 7

The goal of this experiment is to integrate the sensing ability of the nanopores with a sorting capability to enable high-purity selection of error-free DNA molecules. The basic sorting circuit is depicted in FIG. 17, featuring a nanopore membrane integrated with a sorting junction, a ~200 picoliter collection chamber for sorted molecules and an access port to introduce PCR buffer. While measuring a molecular translocation through the nanopore, a low (~300-500 mV) voltage is applied between the input (a) and ground (b). This applied voltage is reversed repeatedly, typically within 250 µs of the previous translocation, in order to perform multiple measurements with large recapture probabilities. The active control algorithm is implemented in real-time using FPGA and rapid-switching relays. Based on the results of Example 5 and Example 6, the devices of the invention enable a determination of whether the molecule under interrogation is error-free or not.

If, based on the translocation signal, the probability of the molecule being correct is less than the target purity, 10V is applied between the ground (b) and waste (c) to reject the molecule (bottom chamber). If MutS causes the DNA to get stuck, the voltage bias across the nanopore is reversed to reject the molecule as described in Example 6. Otherwise, the voltage is applied between the ground (b) and selection sides (d) to direct the likely error-free molecule to the collection chamber. During this time, the voltage bias across the nanopore is floated. Separate control experiments with fluorescent dyes and labeled DNA molecules are performed to compare expected DNA travel times to the collection chamber with first principles estimates. After waiting long enough for the molecule to reach either collection chamber, the process is repeated. Following the sorting operation, a PCR mixture is injected into the device (FIG. 17, top port) to rinse the selected DNA into the microchannel port, and the DNA sample from the device is transferred into an external thermocycler.

Digital PCR has demonstrated the ability to detect DNA down to 1-10 molecules (Nakano, M. et al., *Journal of Biotechnology*, 2003, 102(2), 117-124; Bhat, S. et al., *Analytical and Bioanalytical Chemistry*, 2009, 394(2), 457-467, each of which is incorporated herein by reference), with commercial digital PCR platforms and recent advances in on-chip PCR (Heyries, K. et al., *Nature Methods*, 2011, 8(8), 649). Performing PCR on a highly purified sample is a useful approach, as the errors induced in synthesis of the DNA molecule exceed that of PCR amplification, theoretically making selection of even a single error-free molecule from a mixture of largely unusable molecules very valuable. For example, if the starting purity of PCA products is as low as 1%, the ability to sort only 10 molecules with 90% confidence represents a 90-fold increase in the purity. PCR is used herein to amplify the sorted sample to working concentrations, converting a failed PCA reaction into one that can be directly used, or at least used after a considerably simplified error correction step. Thus, this capacity enables useful products to be extracted from complex impure mixtures, and also provides insurance against common reaction-to-reaction variations in synthesis success. A 2406 bp DNA product encoding the gene for MutS from *Thermotoga maritima* will be synthesized, a length very challenging to synthesize with high purity, in a single step. Using standard methods, typically, only 1.8% of the DNA product is accurately synthesized. Following purification by the nanopore sensor and PCR, the improvement in error rates are quantified using gel electrophoresis and EMSA (see Example 5 and Example 6).

This example develops a tool for on chip single molecule sorting using electronic measurements instead of optical measurements. To gauge whether DNA loss is an issue, a fixed number of identical DNA molecules is passed through the nanopore into the collection chamber, and whether the sample can be successfully withdrawn and amplified is measured. Should adsorption of DNA molecules to device surfaces be a challenge, 10% DMSO can be included in the solution for elution or during sorting. DMSO has been shown to eliminate electrostatic adhesion of DNA (Shin, Y. S. et al., *Chemphyschem* 2010, 11, (14), 3063-3069, incorporated herein by reference). If required, surface passivation can be performed on the device (e.g., dynamic coatings such as n-dodecyl β-maltoside (Kong, D. S. et al., *Nucleic Acids Research*, 2007, 35(8), e61, incorporated herein by reference), or covalent functionalization such as PEG-silane (Demming, S. et al., *Physica Status Solidi a-Applications and Materials Science*, 2011, 208(6), 1301-1307, incorporated herein by reference)), and DNA adhesion can be measured using a Quartz Crystal Microbalance. The sorting performance are tested using dsDNA molecules with two different lengths, e.g., 1 kbp and 10 kbp, which can be easily distinguished in the nanopore. The two molecules are stained with two different intercalating dyes. After sorting for selection of one of the molecules, the two outlet microchannels are imaged, and the sorting performance are quantified in terms of the purity.

Summary

In summary, provided here are integrated nanopores within complex microfluidic networks that can operate with low noise, manipulate fluid transport between layers, and sense single molecules (e.g., DNA molecules) with high fidelity. The devices are fabricated (i.e., produced) using a modular process that relies on transfer printing, whereby nanopores in solid-state ultrathin membranes are registered between microfluidic channels. One of the rate-limiting aspects of current nanopore research has been bridging microfluidic systems with nanopore sensors and as such, these findings have significant implications for nanopore usage in new formats that were previously unattainable with single point nanopore measurements.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device comprising
a first substrate comprising at least one microchannel,
a second substrate comprising at least one microchannel, the second substrate positioned below the first substrate, and
a membrane having a thickness of about 0.3 nm to about 1 µm and comprising at least one nanopore, the membrane positioned between the first substrate and the second substrate,
wherein a nanopore of the membrane is constructed and arranged for electrical and fluid communication at an intersection between a microchannel of the first substrate and a microchannel of the second substrate, wherein a substantially horizontal axis of a microchannel of the first substrate is positioned at an angle of about 10° to about 90° relative to a substantially horizontal axis of a microchannel of the second substrate.

2. The device of claim 1, wherein the membrane has a thickness of about 0.3 nm to about 500 nm.

3. The device of claim 1, wherein one side of the membrane has a surface area of about 10 µm×10 µm to about 10 mm×10 mm.

4. The device of claim 1, wherein the membrane is a dielectric membrane.

5. The device of claim 4, wherein the dielectric membrane is a silicon nitride (SiNx) dielectric membrane.

6. The device of claim 1, wherein the membrane is coated with a semiconductor material.

7. The device of claim 6, wherein the semiconductor material is at least one of alumina ($Al_2O_3$), silicon dioxide ($SiO_2$), hafnium dioxide ($HfO_2$), titanium dioxide ($TiO_2$), graphene, hexagonal boron nitride (hBN), zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$.

8. The device of claim 1, wherein a microchannel of the first and/or second substrate has an inlet at a first end and an outlet at a second end.

9. The device of claim 8, further comprising a negative electrode at the inlet of a microchannel of the first substrate, and a positive electrode at the outlet of a microchannel of the second substrate.

10. The device of claim 1, wherein the first and/or second substrate comprises 2 to 2000 microchannels.

11. The device of claim 1, wherein a microchannel of the first and/or second substrate is a substantially linear microchannel or has a branched portion at one or more ends.

12. The device of claim 11, wherein the branched portion comprises 2 to 20 microchannels.

13. The device of claim 1, wherein a microchannel of the first and/or second substrate has a collection chamber at one or more ends.

14. The device of claim 1, wherein the device comprises at least one access port.

15. The device of claim 1, wherein the central portion of a microchannel of the first and/or second substrate has a width of about 100 nm to about 1 mm.

16. The device of claim 1, wherein the at least one nanopore of the membrane has a diameter of about 0.2 nm to about 1 µm and a length of about 0.3 nm to about 1 µm.

17. The device of claim 1, wherein the at least one nanopore of the membrane has a diameter that is constructed and arranged for translocation from one microchannel to another microchannel of a nucleic acid molecule that is 20 nucleotides to $10^6$ nucleotides in length.

18. The device of claim 17, wherein the nucleic acid molecule is a single-stranded nucleic acid molecule or a double-stranded nucleic acid molecule.

19. The device of claim 1, wherein the membrane comprises 2 to 10000 nanopores.

20. The device of claim 1, wherein each substrate comprises a polymer or a non-polymer.

21. The device of claim 20, wherein each substrate comprises a polymer that comprises silicone, polydimethylsiloxane (PDMS), polycarbonate, poly(methyl methacrylate), zeonax, cyclic olefin polymer (COP), polyester toner (PeT) and cellulose.

22. The device of claim 20, wherein each substrate comprises a non-polymer that comprises glass, silica, silicon, nitride, paper, gallium arsenide or germanium.

23. The device of claim 1, wherein the first and/or second substrate comprises at least one surface modification selected from the group consisting of a crosslinking agent, a silane group, an adhesive coating and plasma.

24. The device of claim 1, wherein one side of the first and/or second substrate has a surface area of about 50 µm² to about 100 mm².

25. The device of claim 1, wherein the surface area of one side of the first substrate is about equal with the surface area of one side of the second substrate.

26. The device of claim 1, wherein the membrane is covalently bonded to the first and/or second substrate.

27. The device of claim 1, wherein the device is connected to a switch, amplifier, digital recorder, computer or a combination thereof.

28. An array comprising 2 to $10^5$ devices of claim 1.

29. A method, comprising adding a plurality of molecules to a microchannel of the first or second substrate of the device of claim 1;
applying an ionic current across the membrane, thereby providing for translocation of a molecule of the plurality of molecules from a microchannel of one substrate to a microchannel of another substrate through a nanopore of the membrane.

30. A device comprising
a first substrate comprising at least one microchannel,
a second substrate comprising at least one microchannel, the second substrate positioned below the first substrate,
a membrane having a thickness of about 0.3 nm to about 1 µm and comprising at least one nanopore, the membrane positioned between the first substrate and the second substrate,
wherein a nanopore of the membrane is constructed and arranged for electrical and fluid communication at an intersection between a microchannel of the first substrate and a microchannel of the second substrate, and
wherein the device further comprises an additional substrate positioned above or below the first and/or second substrate, the additional substrate comprising
at least one microchannel;
an additional membrane having a thickness of about 0.3 nm to about 1 µm and comprising at least one additional nanopore;
an additional membrane having a thickness of about 0.3 nm to about 1 µm disposed between an additional substrate and the first and/or second substrate, wherein the additional membrane comprises at least one additional nanopore; or
one or more valves.

31. A method comprising
providing a first substrate comprising at least one microchannel, wherein a membrane having a thickness of about 0.3 nm to about 1 µm and comprising at least one nanopore is disposed on a surface of the first substrate such that the at least one nanopore of the membrane contacts the microchannel of the first substrate;
providing a second substrate comprising at least one microchannel; and
contacting the membrane with the second substrate, wherein a nanopore of the membrane provides electrical and fluid communication between the microchannel of the first substrate and the microchannel of the second substrate, wherein a substantially horizontal axis of a microchannel of the first substrate is positioned at an angle of about 10° to about 90° relative to a substantially horizontal axis of a microchannel of the second substrate.

32. A method comprising
depositing a membrane having a thickness of about 0.3 nm to about 1 µm on an initial substrate;
forming at least one nanopore in the membrane;
contacting the membrane with a surface of a first substrate having at least one microchannel such that the at least one nanopore of the membrane contacts the at least one microchannel of the first substrate;
removing the initial substrate from contact with the membrane; and
contacting the membrane with a second substrate having at least one microchannel,
wherein the at least one nanopore of the membrane provides electrical and fluid communication between the at least one microchannel of the first substrate and the at least one microchannel of the second substrate, and wherein a substantially horizontal axis of a microchannel of the first substrate is positioned at an angle of about 10° to about 90° relative to a substantially horizontal axis of a microchannel of the second substrate.

* * * * *